United States Patent [19]
Lee et al.

[11] Patent Number: 5,858,771
[45] Date of Patent: Jan. 12, 1999

[54] PRODUCTS AND METHODS FOR CONTROLLING THE SUPPRESSION OF THE NEOPLASTIC PHENOTYPE

[75] Inventors: Wen-Hwa Lee; Huei-Jen Su Huang; Eva Y. H. P. Lee, all of San Diego, Calif.

[73] Assignee: The Regents of the University of California, Oakland, Calif.

[21] Appl. No.: 337,855

[22] Filed: Nov. 14, 1994

Related U.S. Application Data

[63] Continuation of Ser. No. 764,714, Sep. 24, 1991, abandoned, which is a continuation of Ser. No. 265,829, Oct. 31, 1988, abandoned, which is a continuation-in-part of Ser. No. 91,547, Aug. 31, 1987, Pat. No. 5,011,773, Ser. No. 98,612, Sep. 17, 1987, Pat. No. 4,942,123, and Ser. No. 108,748, Oct. 15, 1987, abandoned.

[51] Int. Cl.$^6$ .................................................. C12N 15/00
[52] U.S. Cl. ........................................ 435/320.1; 536/23.1
[58] Field of Search ........................ 536/23.1; 435/172.3, 435/240.2, 320.1; 514/44; 424/93.1; 935/62; 800/2, DIG. 1–3

[56] References Cited

U.S. PATENT DOCUMENTS

| | | |
|---|---|---|
| 4,497,796 | 2/1985 | Salser et al. ............................ 424/93.1 |
| 5,532,220 | 7/1996 | Lee et al. .................................. 514/44 |

FOREIGN PATENT DOCUMENTS

WO 89/06703   7/1989   WIPO .............................. C12Q 1/68

OTHER PUBLICATIONS

Friedman, Cancer Supp. 70(6) : 1807–1817 (1992).
Angier, N., *Discover* Mar.:85–96 (1987).
Benedict et al., *Cancer Genet. and Cytogenet.* 10:311–333 (1983).
Benedict et al., *Science* 219:973–975 (1983).
Bender et al., *J. Mol. Biol.* 168:17–33 (1983).
Bookstein et al., *Proc. Natl. Acad. Sci. USA* 85:2210–2214 (1988).
Bookstein et al., *Science* 247:712–715 (1990).
Cavenee et al., *Am. J. Hum. Genet.* 36:10–24 (1984).
Cavenee et al., *Nature* 305:770–784 (1983).
Cepko et al., *Cell* 37:1053–1062 (1984).
Dryja et al., *Proc. Natl. Acad. Sci. USA* 83:7391–7394 (1986).
Friend et al., *Nature* 323:643–646 (1986).
Friend et al., *Proc. Natl. Acad. Sci USA* 84:9059–9063 (1987).
Fung et al., *Science* 236:1657–1661 (1987).
Gossler et al., *Proc. Natl. Acad. Sci. USA* 83:9065–9069 (1986).
Harris, Henry, *Nature* 323:582–583 (1986).
Hooper et al., *Nature* 326:292–295 (1987).
Kantoff et al., *Proc. Natl. Acad. Sci. USA* 83:6563–6567 (1986).
Kuehn et al., *Nature* 326:295–298 (1987).
Lee et al., *Nature* 329:642–645 (1987).
Lee et al., *Proc. Natl. Acad. Sci. USA* 83:6337–6341 (1986).
Lee et al., *Proc. Natl. Acad. Sci. USA* 83:6790–6794 (1986).
Lee et al., *Proc. Natl. Acad. Sci. USA* 85:6017–6021 (1988).
Lee et al., *Science* 235:1394–1399 (1987).
Lee et al., *Science* 241:218–221 (1988).
Mann et al., *Cell* 33:153–159 (1983).
Miller et al., *Molecular and Cellular Biol.* 5(3): 431–437 (1985).
Miller et al., *Proc. Natl. Acad. Sci. USA* 80:4709–4713 (1983).
Miller et al., *Cold Spring Harbor Symposia on Quantitative Biology* LI:1013–1019 (1986).
Murphree et al., *Science* 223:1028–1033 (1984).
Shew et al., *Oncogene Research* 1:205–214 (1989).
Strong et al., *Science* 213:1501–1503 (1981).
Thomas et al., *Cell* 44:419–428 (1986).
Weissman et al., *Science* 236:175–180 (1987).
Vieweg et al. "Considerations for the Use of Cytokine–Secreting Tumor Cell Preparations for Cancer Treatment," Cancer Investigation, vol. 13 (2):192–201, 1995.
Vieweg et al. "Immunotherapy of Prostate Cancer in the Dunning Rat Model: Use of Cytokine Gene Modified Tumor Vaccines," Cancer Research, vol. 54:1760–1765, Apr. 1994.
Miller, A.D. "Progress Toward Human Gene Therapy," Blood, vol. 76(2):271–278, Jul. 1990.
Roemer et al. "Concepts and strategies for human gene therapy," Eur. J. Biochem., vol. 208:211–225, 1992.

*Primary Examiner*—Jasemine C. Chambers
*Assistant Examiner*—Karen M. Hauda
*Attorney, Agent, or Firm*—Townsend and Townsend and Crew

[57] ABSTRACT

A method for gene therapy for cancers wherein chromosomal location of an inactive or defective cancer suppressing gene is established, a replacement gene which is preferably cloned is then used to replace the inactive or defective cancer suppressing gene in the chromosome. In addition to its uses in therapy, the present invention provides a means for prophylactically treating individuals having a genetic predisposition to cancer and provides an animal model for testing for carcinogenicity of environmental substances.

6 Claims, 11 Drawing Sheets

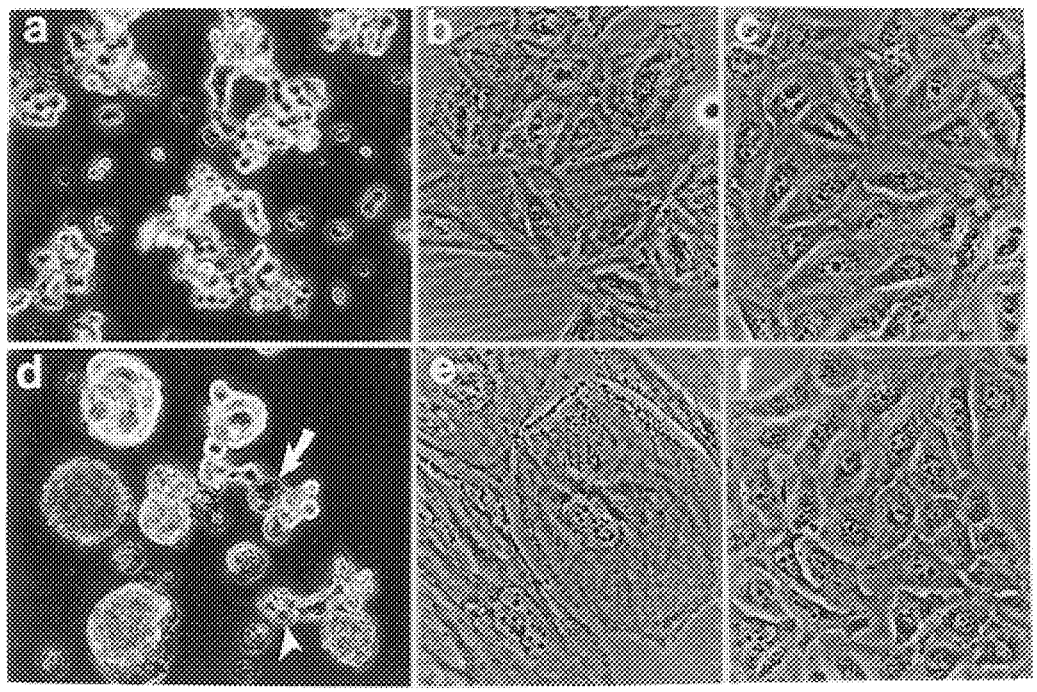

MPPKTPRKTAATAAAAAEPPAPPPPPEEDPEQDSGPEDLPL
VRLEFEETEEPDFTALCQKLKIPDHVRERAWLTWEKVSSVDGVLGGYIQKKELWGIC
IFIAAVDLDEMSFTFTELQKNIEISVHKFFNLLKEIDTSTKVDNAMSRLLKKYDVLFA
LFSKLERTCELIYLTQPSSSISTEINSALVLKVSWITFLLAKGEVLQMEDDLVISFQL
MLCVLDYFIKLSPPMLLKEPYKTAVIPINGSPRTPRRGQNRSARIAKQLENDTRIIEV
LCKEHECNIDEVKNVYFKNFIPFMNSLGLVTSNGLPEVENLSKRYEEIYLKNKDLDAR
LFLDHDKTLQTDSIDSFETQRTPRKSNLDEEVNVIPPHTPVRTVMNTIQQLMMILNSA
SDQPSENLISYFNNCTVNPKESILKRVKDIGYIFKEKFAKAVGQGCVEIGSQRYKLGV
RLYYRVMESMLKSEEERLSIQNFSKLLNDNIFHMSLLACALEVVMATYSRSTSQNLDS
GTDLSFPWILNVLNLKAFDFYKVIESFIKAEGNLTREMIKHLERCEHRIMESLAWLSD
SPLFDLIKQSKDREGPTDHLESACPLNLPLQNNHTAADMYLSPVRSPKKKGSTTRVNS
TANAETQATSAFQTQKPLKSTSLSLFYKKVYRLAYLRLNTLCERLLSEHPELEHIIWT
LFQHTLQNEYELMRDRHLDQIMMCSMYGICKVKNIDLKFKIIVTAYKDLPHAVQETFK
RVLIKEEYDSIIVFYNSVFMQRLKTNILQYASTRPPTLSPIPHIPRSPYKFPSSPLR
IPGGNIYISPLKSPYKISEGLPTPTKMTPRSRILVSIGESFGTSEKFQKINQMVCNSD
RVLKRSAEGSNPPKPLKKLRFDIEGSDEADGSKHLPGESKFQQKLAEMTSTRTRMQKQ
KMNDSMDTSNKEEK

Fig. 6A

```
   1 ttccggtttt tctcagggga cgttgaaatt attttgtaa cgggagtcgg gagaggacgg
  61 ggcgtgcccc gcgtgcgcgc gcgtcgtcct cccgcgct cctccacagc tcgctggctc
 121 ccgccgcgga aaggcgtcat gccgcccaaa acccgccgc aaacggccgc caccgccgcc
 181 gctgccgccg cggaaccccg ggcaccgccg ccgccgccg ctccgtagga ggacccagag
 241 caggacagcg gcccgagga cctgcctctc gtcaggcttg agtttgaaga aacagaagaa
 301 cctgatttta ctgcattatg tcagaaatta aagataccag atcatgtcag agagagagct
 361 tggttaactt gggagaaagt ttcatctgtg gatggagtat tggaggtta tattcaaaag
 421 aaaaaggaac tgtgggaat ctgtatcttt attgcacgag ttgacctaga tgagatgtcg
 481 ttcactttat ctgagctaca gaaaaacata gaaatcagtg tccataaatt ctttaactta
 541 ctaaaagaaa ttgataccag taccaaagtt gataatgcta tgtcaagact gttgaagaag
 601 tatgatgtat tgtttgcact cttcagcaaa ttggaaagga catgtgaact tatatatttg
 661 acacaaccca gcagttcgat atctactgaa ataaattctg cattggtgct aaaagttctt
 721 tggatcacat ttttattagc taaaggggaa gtattacaaa tggaagatga tctggtgatt
 781 tcattttcagt taatgctatg tgtccttgac tattttatta aactctcacc tcccatgttg
 841 ctcaaagaac catataaaac agctgttata cccattaatg gttcacctcg aacacccagg
 901 cgaggtcaga acaggagtgc acggatagca aaacaactag aaaatgatac aagaattatt
 961 gaagttctct gtaaagaaca tgaatgtaat atagatgagg tgaaaaatgt ttatttcaaa
1021 aatttatac cttttatgaa ttctcttgga cttgtaacat ctaatggact tccagaggtt
1081 gaaaatcttt ctaaacgata cgaagaaatt tatcttaaaa ataaagatct agatgcaaga
1141 ttattttgg atcatgataa aactcttcag actgattcta tagacagttt tgaaacacag
1201 agaacaccac gaaaagtaa ccttgatgaa gaggtgaatg taattcctcc acacactcca Fig. 6B
```

```
1261 gttaggactg ttatgaacac tatccaacaa ttaatgatga ttttaaattc agcaagtgat
1321 caaccttcag aaaatctgat ttcctatttt aacaactgca cagtgaatcc aaagaaagt
1381 atactgaaaa gagtgaagga tataggatac atctttaaag agaaatttgc taaagctgtg
1441 ggacaggttt gtgtcgaaat tggatcacag cgatacaaac ttggagttcg cttgtattac
1501 cgagtaatgg aatccatgct taaatcagaa gaagaacgat tatccattca aaattttagc
1561 aaacttctga atgacaacat ttttcatatg tcttttattg cgtgcgctct tgaggttgta
1621 atggccacat atagcagaag tacatctcag aatcttgatt ctggaacaga tttgtctttc
1681 ccatggattc tgaatgtgct taattaaaaa gcctttgatt tttacaaagt gatcgaaagt
1741 tttatcaaag cagaaggcaa cttgacaaga gaaatgataa aacatttaga acgatgtgaa
1801 catcgaatca tggaatccct tgcatggctc tcagattcac ctttatttga tcttattaaa
1861 caatcaaagg accgagaagg accaactgat cacctttgaat ctgcttgtcc tcttaatctt
1921 cctctccaga ataatcacac tgcagcagat atgtatcttt cactgtttta atctccaaag
1981 aaaaaaggtt caactacgcg tgtaaattct actgcaaatg acctctcttt cagagacaca agcaacctca
2041 gccttccaga cccagaagcc attgaaatct acctctcttt cttgtgaac gccttctgtc taaaaaagtg
2101 tatcggctag cctatctccg gctaaataca gacccttttc cagcacaccc tgcagaatga gtatgaactc
2161 gaattagaac atatcatctg gacccttttc ccaaattatg atgtgttcca tgtatggcat atgcaaagtg
2221 atgagagaca ggcatttgga ccaaattatg atgtgttcca tgtatggcat atgcaaagtg
2281 aagaatatag accttaaatt caaaatcatt gtaacagcat acaaggatct tcctcatgct
2341 gttcaggaga cattcaaacg tgttttgatc aaagaagagg agtatgattc tattatagta
2401 ttctataact cggtcttcat gcagagactg aaaacaaata tttgcagta tgcttccacc
2461 aggcccccta ccttgtcacc aatacctcac attcctcgaa attcctacaa gccttacaa gttcctagt
```

Fig. 6C

```
2521  tcacccttac ggattcctgg agggaacatc tatatttcac ccctgaagag tccatataaa
2581  atttcagaag gtctgccaac accaacaaaa atgactccaa gatcaagaat cttagtatca
2641  attggtgaat cattcgggac ttcctgagaag ttccagaaaa taaatcagat ggtatgtaac
2701  agcgaccgtg tgctcaaaag aagtgctgaa ggaagcaacc ctcctaaacc actgaaaaaa
2761  ctacgctttg atattgaagg atcagatgaa gcagatggaa gtaaacatct cccaggagag
2821  tccaaatttc agcagaaact ggcagaaatg acttctactc gaacacgaat gcaaaagcag
2881  aaaatgaatg atagcatgga tacctcaaac aaggaagaga aatgaggatc tcaggacctt
2941  ggtggacact gtgtacacct ctggattcat tgtctctcac agatgtgact gtat
```

Fig. 6D

PRODUCTS AND METHODS FOR CONTROLLING THE SUPPRESSION OF THE NEOPLASTIC PHENOTYPE

CROSS REFERENCES TO RELATED APPLICATIONS

This application is a continuation of application Ser. No. 07/764,714, filed Sep. 24, 1991, (now abandoned) which is a continuation of U.S. Ser. No. 07/265,829 filed Oct. 31, 1988, (now abandoned); which is a continuation-in-part of U.S. Ser. No. 091,547 filed Aug. 31, 1987 (patent issued: U.S. Pat. No. 5,011,773); U.S. Ser. No. 098,612 filed Sep. 17, 1987 (patent issued: U.S. Pat. No. 4,942,123); and U.S. Ser. No. 108,748 filed Oct. 15, 1987 (abandoned).

This invention was made with Government support under Grant No. EY05758 with the National Institute of Health, and the University of California. The Government has certain rights in this invention.

TECHNICAL FIELD

This invention relates in general to products and methods for the therapeutic and prophylactic treatment of mammals, to control the phenotypic expression of cancer, and to the production of products and methods for testing for carcinogenicity of environmental substances.

BACKGROUND ART

For many years, cancer in its numerous forms, has been a frightful bane to human society. In many cases, the condition is discovered when the pathological condition has advanced to the point that the patient's life cannot be saved, and the fatal progress of the disease cannot be reversed.

Some cancerous conditions, if diagnosed and treated in a timely fashion, may be arrested with the life of the patient thereby prolonged. It is the hope of this outcome that motivates cancer patients to spend substantial amounts of money on varying forms of cancer treatment. Because cancer attacks the organism at the elementary, cellular level, through the uncontrolled proliferation of cells, the treatment of cancer has been, historically, dramatic and often destructive of the organism.

In effect, many treatments for cancer, because they are intended to function dramatically at the cellular level, sometimes themselves destroy healthy cells. Often, destruction of a sufficient number of healthy cells has contributed to, if not caused, death of the patient. Nevertheless, since the patient has only the prospect of imminent death as an alternative, drastic, expensive and life-threatening treatments, such as X-radiation and chemotherapy, have been employed.

Even when such treatment is successful, the cancer patient remains disabled and ill for significant periods of time after treatment has ceased. Generally, the patient requires hospitalization, not only during the period of treatment, but for significant times thereafter.

For these reasons, the spectre of cancer has caused great fear in human society. The economic impact, in terms of cost of medical care, combined with the disabling effect of the disease on its sufferers have made the search for reliable methods of diagnosing not only the disease but a predisposition to it, and of treating the disease and/or causing its predisposition very significant.

Much of the focus of cancer research has been on the diagnosis and treatment of the condition. In recent years, because of advances in knowledge of biochemical processes at the cellular and subcellular level, attention has been directed to methods, not only for diagnosing and treating cancer, but also for discovering a predisposition for cancer in the organism. In order to determine such a predisposition, studies have been done to determine the mechanisms in the body for suppressing cancer.

In these studies, "cancer suppression" was originally defined by a loss of tumorigenicity observed in fusion cells made with tumor cells and normal fibroblasts, lymphocytes or keratinocytes. The effect was presumed to be mediated by dominant suppressive factors in normal cells, Nature 223:363 (1969) and J. Cell Sci. 8:659 (1974).

Evidence indicated that these factors were in part genetic since a correlation existed between suppression of tumorigenicity and the presence of certain chromosomes in fused cells, Adv. Viral Oncol. 6:83 (1987). For example, Wilms tumor, a childhood tumor of the kidney, is thought to arise by inactivation of a gene on chromosome 11. Using the technique of microcell fusion-mediated transfer of single chromosomes, it has been demonstrated that introduction of a normal chromosome 11 into Wilms tumor cells suppressed their tumorigenicity. On the other hand, the introduction of chromosomes X and 13 did not have this effect, Science 236:175 (1987).

However, since entire human chromosomes were transferred, cancer suppression could not be attributed to molecularly defined genetic elements. In addition, the transfer of entire human chromosomes may present significant problems when attempted on a basis other than experimental. The preparation of suitable chromosomes for therapeutic applications is very exacting, time-consuming and expensive. As a result, such a technique has not been found to be acceptable for many applications. For these reasons, it would be highly desirable to have a method of accomplishing cancer treatment biotechnically, both therapeutically and prophylactically, which would overcome such problems associated with the introduction of chromosomes to the patient.

Another meaning for cancer suppressing genes arose in connection with genetic studies on certain childhood neoplasms, Cancer 35:1022 (1975) and Nature 316:330 (1985) and adult tumor syndromes Nature 328:614 (1987); ibid 332:85 (1988); ibid 329:246 (1987); ibid 322:644 (1986). Genes contributing to the formation of these tumors appear to be oncogenic by loss of function, rather than activation, as with the classical oncogenes, Science 235:305 (1987); ibid 238:1539 (1987); Nature 323:582 (1986); Cancer Res. 46:1573 (1986).

Retinoblastoma, a childhood eye cancer, provides the prototypic example, J. Cell. Biochem. in press (1988). Refined cytogenetic analyses, Am. J. Dis. Child. 132:161 (1978); Science 208:1042 (1980); J. Med. Genet. 21:92 (1984) and study of restriction fragment length polymorphisms (RFLPs), Nature 305:779 (1983) suggested that retinoblastoma may result from loss of a gene locus, called RB or RB-1, located in chromosome band 13q14. A gene from this region possessing properties consistent with the RB gene, has been molecularly cloned, Nature 323:643 (1986); Science 235:1394 (1987), and ibid 236:1657 (1987). Expression of this gene as a 4.7 kb mRNA transcript was found in all normal tissues examined, but was undetectable or altered in retinoblastoma cells, Science 235:1394 (1987), and the mutations within the RB gene have been identified in many cases Science, 236:1657 (1987), and Proc. Natl. Acad. Sci. 85:2210 (1988) and ibid 85:6017 (1988). This data suggested that the cloned RB gene was tentatively identified.

A protein product of the RB gene was previously identified as a nuclear phosphoprotein of about 110 kd (pp110$^{RB}$) using antibodies generated against selected epitomes predicted from the RB cDNA sequence, Nature 329:642 (1987).

In light of the evidence establishing the cancer suppression properties of the RB gene, work has been done to utilize the RB gene in the determination of the susceptibility to retinoblastoma as a diagnostic tool. These diagnostic methods and products are disclosed in pending U.S. patent application Ser. No. 108,748, which describes cloning, isolation, identification and sequencing of the RB gene. In addition, said patent application also discloses the method of use of the cloned retinoblastoma gene cDNA as a tool for diagnosing retinoblastoma, osteosarcoma and fibrosarcoma.

Additionally, pending U.S. patent application Ser. No. 098,612, discloses a phosphoprotein ppRB$^{110}$ which is primarily located in the cell nucleus and has DNA binding activity. As with RB mRNA, this protein was detected in many types of cultured human cells. pp110$^{RB}$ has been shown to form a tight association with large T antigen and E1A, the transforming proteins of DNA tumor viruses SV40 and adenovirus respectively, Nature 334:124 (1988); Cell 54:275 (1988). The RB gene product, or a complex containing it, has been found to have DNA binding activity, Nature 329:642 (1987). These studies indirectly suggested that pp110$^{RB}$ has a role in regulating the expression of other cellular genes, and may also mediate the oncogenic effects of some viral transforming proteins.

Much of the current cancer research is directed toward the detection and a predisposition in the organism toward development of cancer. Therefore, it would be highly desirable if a prophylactic method of cancer treatment existed so that tumorigenesis could be arrested before its inception or, even more importantly, foreclosed from development altogether.

In this regard, in pending U.S. application Ser. No. 091,547, there is described methods for using cloned human esterase D cDNA as a genetic marker as a diagnostic tool for retinoblastoma, Wilson's disease, and other hereditary or acquired diseases controlled by genes located at the 13 chromosome 13q:1411 region. The patent application discloses an esterase D cDNA probe for cloning the retinoblastoma gene, and the use of the cloned human esterase cDNA as a prognostic tool for determination of genetic predisposition to retinoblastoma or Wilson's disease.

Thus, although significant advances are being made in the development of prognostic tools for determination of the genetic predisposition to cancer, therapeutic and prophylactic treatment of cancer still present the serious foregoing-mentioned limitations. In this regard, the prognostic tool is extremely useful in screening a population, to determine which persons may have a predisposition toward cancer. Thus, once a person is determined by means of the diagnostic tool as having such a predisposition, the person can be monitored at short intervals for the early signs and symptoms of cancer. If such is found, appropriate procedures, such as surgery, can be undertaken at an early date.

However, while the use of diagnostic tools for the predisposition toward cancer is highly advantageous, the knowledge of such a predisposition is not helpful in the situation where a patient is determined by conventional examination techniques to have, for example, an advanced stage of cancer. In these cases, conventional procedures and treatments have not proven to be entirely satisfactory.

Therefore, it would be highly desirable to have prophylactic and/or therapeutic treatments for cancer, by utilizing biotechnical techniques. Moreover, it would be important to have such biotechnical modalities, which are effective for many different forms of cancer, with little or no side effects. It would also be desirable to have techniques for proving that certain environmental substances, such as cigarette smoke, cause cancer. Having this type of information could also be used to help people avoid coming into contact with cancer causing substances, since these substances would be proven, rather than merely suspected, of playing a role in oncogenesis.

DISCLOSURE OF INVENTION

It is a primary object of this invention to provide generally safe and specific therapeutic and prophylactic methods and products useful for controlling cancer suppression.

It is a further object of this invention to provide products and methods of controlling cancer suppression which are specific for eradication of the cancer tumor by utilizing biotechnical methods and products.

It is a still further object of the present invention to provide a pharmaceutical composition for therapeutic treating or prophylactic treating of cancer whose active ingredient consists of a natural or replacement gene.

It is still another object of this invention to provide a pharmaceutical composition for treating and/or prophylactic treatment of cancer whose active ingredient consists of a natural and/or replacement cancer suppressing gene.

It is still another object of this invention to provide a pharmaceutical composition for treating and/or prophylactic treatment of animals having retinoblastoma or genes having defective, mutant or absent RB genes wherein the active ingredient is a natural and/or cloned replacement non-defective RB gene or gene fragment.

It is still another object of the present invention to provide animal models which have defective, mutative or absent cancer suppressing genes.

It is still another object of the present invention to provide methods and products for determining that certain agents and substances cause cancer.

The present invention comprises a method for gene therapy for cancers wherein chromosomal location of an inactive or defective cancer suppressing gene is established. A replacement gene which is preferably cloned is then used to replace the inactive or defective cancer suppressing gene in the chromosome. In addition to its uses in therapy, the present invention provides a means for prophylactically treating individuals having a genetic predisposition to cancer and provides an animal model for testing for carcinogenicity of environment influences. The term "influences," as used herein, is intended to be interpreted in a broad sense so that the term includes, but is not limited to, various forms of radiation and various types of substances found in the environment.

The present invention provides a method of treating cancer which reduces the need for radiation and/or chemotherapy. In addition, it may be employed at a very early stage, after a genetic predisposition to cancer has been discovered, but before the onset of tumorigenesis.

A further advantage of the present invention is that it utilizes genetic materials which are smaller than entire chromosomes and are generally more stable and more easily clone.

In the invention of the composition and method herein disclosed it was hypothesized that if the neoplastic behavior of tumor cells were suppressed by an intact RB gene, RB gene inactivation could then be strongly imputed as an important event during tumorigenesis.

While there is some uncertainty as to whether inactivation of one or more cancer suppressing genes in a cell is sufficient to cause cancer, replacement of inactivated suppressing genes in tumor cells is a novel approach for the treatment of malignancy. Unlike conventional, cytotoxic cancer therapies, gene therapy is premised on permanent correction of an underlying defect in tumor cells. Further, gene therapy may be utilized prophylactically because cancer suppressing genes do not harm normal cells.

BRIEF DESCRIPTION OF FIGURES

The above mentioned and other objects and features of this invention and the manner of attaining them will become apparent, and the invention itself will be best understood by reference to the following description of the embodiment of the invention in conjunction with the accompanying figures wherein:

FIGS. 3A–F shows cultures of RB and Lux virus infected tumor cells after G418 selection;

FIGS. 6A–D shows the amino acid and nucleotide sequence of the RB protein and cDNA, respectively.

BEST MODE FOR CARRYING OUT THE INVENTION

Figure 1A:
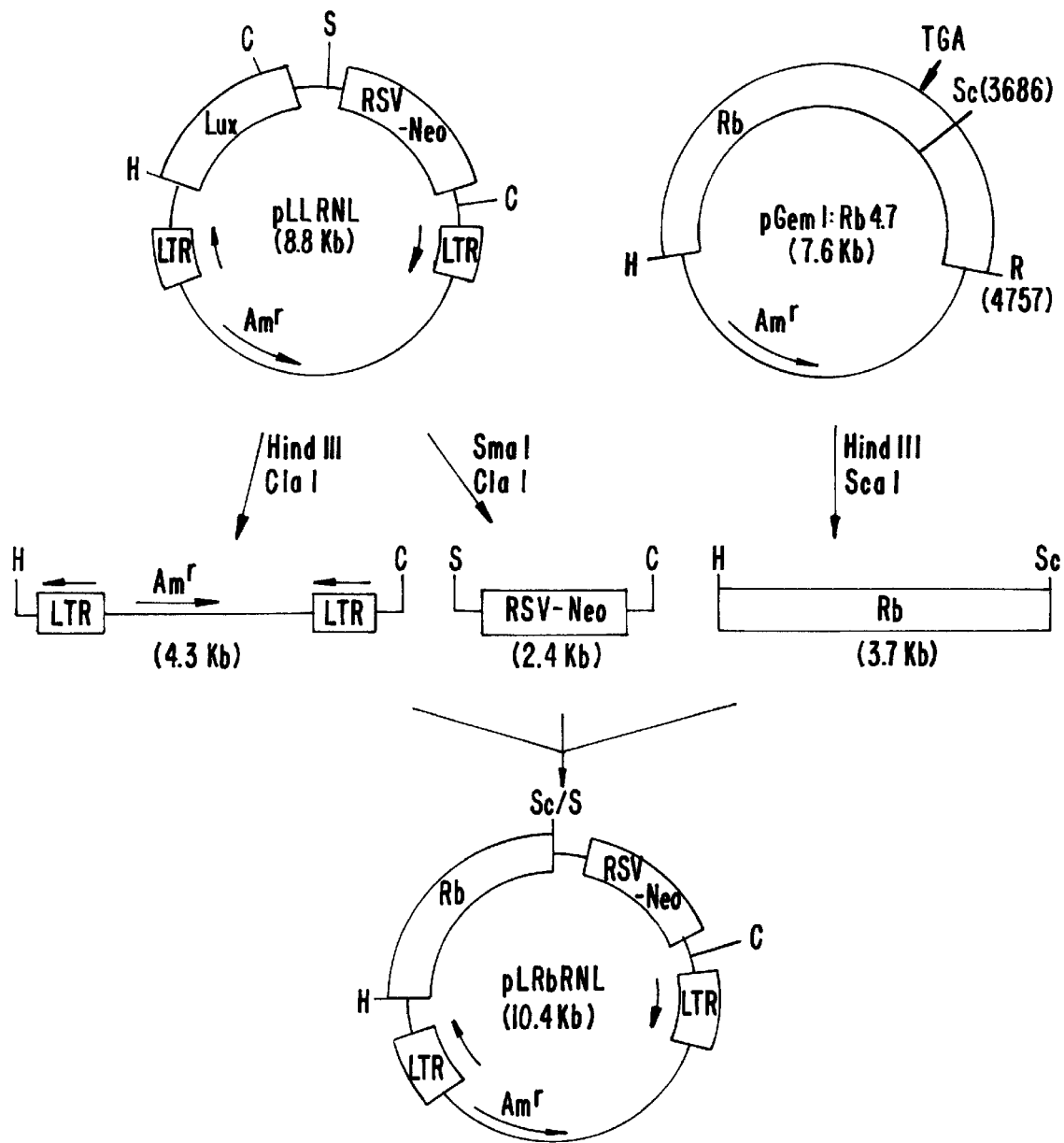
FIG. 1A and FIG. 1B show the method of production of the Rb virus and the Lux virus.

All references cited in this application are hereby incorporated by reference and made part of this application.

The detailed description is arranged according to the following outline:
A. INTRODUCTION
B. INITIAL STEP OF IDENTIFYING CANCER SUPPRESSING GENES
  B1. IDENTIFICATION OF THE MARKER GENE
  B2. MAPPING OF THE ESD GENE
  B3. CLONING THE ESTERASE D GENE
C. GENETICS OF ONCOGENICITY AND CLONING OF CANCER SUPPRESSING GENE
  C1. GENETICS OF RETINOBLASTOMA
  C2. MOLECULAR CLONING OF GENES
  C3. IDENTIFICATION OF THE RB GENE BY CHROMOSOME WALKING
  C4. THE RB GENE IN OTHER CANCERS
  C5. CLONING THE RB GENE
  C6. ONCOGENICITY BY MUTANT RB GENES
D. DIAGNOSTIC PROCEDURES UTILIZING CANCER SUPPRESSING GENE PRODUCTS
  D1. DIAGNOSTIC PROCEDURES FOR DETERMINING CANCER PREDISPOSITION
  D2. IDENTIFICATION AND FUNCTION OF THE RB PROTEIN
  D3. LOCALIZATION AND FUNCTION OF THE ppRB$^{110}$
  D4. REGULATORY FUNCTION OF ppRB1$^{10}$
  D5. ppRB$^{110}$ AS A DIAGNOSTIC TOOL
E. GENE THERAPY AND PROPHYLAXIS
  E1. PRODUCTION OF Rb AND LUX VIRUS INFECTION OF TUMOR CELL LINES
  E2. USE OF THE RB GENE IN CANCER SUPPRESSION
  E3. SUPPRESSION OF ONCOGENICITY IN VITRO AND IN VIVO BY THE RB GENE
  E4. TRANSFORMATION BY INACTIVATION OF RB GENES
F. ANIMAL MODELS FOR EVALUATING SUSPECTED ENVIRONMENTAL INFLUENCE CARCINOGENICITY

A. INTRODUCTION

The present invention relates to the diagnosis and treatment of cancer as well as providing techniques for determining carcinogenicity of environmental influences. The diagnostic techniques of the present invention are based on determining the susceptibility of a patient to cancer, in some cases before a cancer phenotype is expressed. In general, the diagnostic methods include determination of the chromosomal locus of a cancer suppressing gene. After the locus has been established, techniques have been devised for determining whether or not the cancer suppressing gene is present or absent, and, if present, whether the cancer suppressing gene is fully functional.

After the locus of the cancer suppressing gene has been established and the gene has been found to be present, the function of the gene can be determined by observation, under controlled circumstances, of the phenotypic expression of the gene. Once technique for evaluating phenotypic expression is to test for the presence of the cancer suppressing gene's product. A preferred technique is to develop an antibody for the gene product which is capable of forming an immunocomplex with the product thereby providing an accurate test for the presence and amount of protein of gene product in a tissue sample.

Also, after the cancer suppressing gene chromosome location has been established, the gene itself can be cloned and subsequently used as a pharmaceutical product according to the therapeutic methods of the present invention. In this regard, the cloned cancer suppressing gene has a utility in addition to its therapeutic applications since it may also be utilized prophylactically. In this regard, cancer suppressing gene function may be determined prior to any expression of the cancer phenotype in the individual and, if gene deficit or absence is determined, a healthy cloned cancer suppressing gene can be utilized prophylactically in the place of the absent or defective gene.

Additionally, the present invention relates to the production of a mouse model which has been genetically altered so that the model can be utilized as a reliable method for evaluating carcinogenicity of environmental influences such as tobacco smoke, food preservatives, sugar substitutes and the like.

The present invention builds upon specific examples the inventions disclosed and claimed in the previously mentioned pending U.S. patent applications. The invention herein disclosed, and those disclosed and claimed in the pending applications, are based on the substantial body of scientific evidence with indicates that carcinogenesis is associated in some manner with genetic alterations and tumor calls. These alterations may be due to mutation, gene inactivation, suppression, deletion or other causes.

While specific, relevant aspects of the pending applications will be discussed in more detail below, it is worthwhile initially to summarize how each represents a progressive step in establishing the foundation for the present invention.

The present invention, and those disclosed in the pending applications, are based on the substantial body of scientific evidence which indicates that carcinogenesis is associated with genetic alterations in tumor cells. These alterations may be due to mutation, gene inactivation, suppression, deletion or other causes.

With genetic alteration as the hypothetical cause of carcinogenesis, it is important to establish the locus and cause of genetic alterations. In addition, it is important to find ways to prevent such genetic alterations by prophylactic measures. Further, the development of models, such as animal models, to test for carcinogenicity of environmental influences would be useful.

Considering now the diagnostic method of the present invention in greater detail, the process began with the identification of the amino acid sequence of human esterase D and the nucleotide sequence of esterase D cDNA. Esterase D is important because its genetic locus coincides with the location of the retinoblastoma gene (RB). Thus, cloned esterase cDNA is useful as a genetic marker and as a diagnostic tool for retinoblastoma, Wilson's disease and other hereditary or acquired diseases controlled by genes located at the 13 chromosome 13q14:11 region.

In addition to its use as a diagnostic tool, cloned esterase cDNA is useful as a probe to clone the RB, and as a prognostic tool for retinoblastoma, Wilson's disease and other diseases controlled by genes located at the 13 chromosome 13q14:11 region.

Because esterase D and the retinoblastoma gene are located in the same chromosomal region, evaluation of RB gene function, and its chromosomal patterns, was possible. By chromosomal walking, using the esterase D cDNA clone as the starting point, the RB gene was isolated and its nucleotide sequence was determined.

It is believed that the RB gene has a regulatory function and that its presence and normal function prevents the development of retinoblastoma. On the other hand, absence, malfunction or inactivation of the RB gene causes the development of, or genetic predisposition and susceptibility to, retinoblastoma. Further, it is believed that RB gene absence, malfunction or inactivation is the primary cause, not only for hereditary and acquired retinoblastoma but for other cancers as well.

Thus, identification of the exact RB gene location and isolation, identification, sequencing and cloning of the RB gene provided a capability for diagnosis and treatment of retinoblastomas and their secondary tumors. It also provided a method for diagnosis and treatment of other cancers related to RB gene function.

Considering further the diagnostic method of the present invention, an advance in the diagnosis of retinoblastoma, and a predisposition toward retinoblastoma and other cancers, occurred with the identification of a phosphoprotein. The phosphoprotein is associated with DNA binding activity located in the nucleus. The phosphoprotein, identified as $ppRB^{110}$, plays a role in inhibiting the oncogenic activity of genes other than the RB gene and, in addition, it restrains malignant cell growth.

The identification, isolation, and determination of the nucleotide sequence and cloning of the RB gene, together with the identification of its phosphoprotein product has many uses.

An important primary utility lies in the capacity for preparing RB gene protein product which can then be used as an antigen in obtaining specific anti-protein antibody. This antibody can be used as a diagnostic immunomarker for the investigation of the presence or absence of the RB gene protein in examined tissue. If the protein is present, the RB gene is intact and retinoblastoma is not present. If, on the other hand, the protein is absent or altered, the deficient RB gene is indicated and resulting retinoblastoma or other cancers or susceptibility to them is diagnosed.

There are now two approaches whereby diagnosis of retinoblastoma and other related cancers can be performed. In the first, the RB cDNA or genomic DNA is used as a probe to determine whether a deficit exists in the chromosomal locus of the RB gene. Alternatively, immunoscreening of tissue biopsy with specific anti-$ppRB^{110}$ antibody is also practical. Both diagnostic methods have application for screening families with a history of hereditary retinoblastoma and for screening of their children. In addition, the methods may be used for prediction of development of secondary cancer, such as osteosarcoma, fibrosarcoma, glioblastoma, breast cancer and others, whether or not connected with retinoblastoma.

Considering now the therapeutic methods of the present invention, tumorigenesis can be suppressed by providing cloned cancer suppressing genes, such as RB genes, or the cancer suppressing gene protein product, such as $ppRB^{110}$, after a defective, inactive or absent cancer suppression gene has been diagnosed. These substances can be provided through molecular induction or gene transplanting of RB cDNA to the individual in need. Thus, these methods, in addition to their prophylactic value, have application to a method of arrest of tumor development in the individual.

Considering further the development of animal modules, in addition to the use of cancer suppressing genes and their related proteins, in diagnostic, prophylactic and therapeutic applications, it is possible to utilize the methods herein disclosed to establish animal models for studying cancer suppressing gene function. As an example, mutant mice have been developed with one inactive allele of the RB gene. These animals are useful in further elucidating the role and significance of the cancer suppressing gene.

In addition, because "heterozygosity" appears to be the condition precedent to tumorigenesis, the mutant mice become useful models in testing for carcinogenicity of environmental substances. Thus, for example, such mice could be exposed to cigarette smoke, artificial sweeteners or a myriad of other suspected carcinogens. Tumor development in the mice would be a positive indication of the carcinogenicity of the substance tested. The availability of the mutant mouse models thus provides a means for determining which environmental substances should be avoided.

In addition to their value as models for testing environmental substances, the mutant mouse models have value in cancer therapy studies.

It should be understood that the basic concepts discussed herein are useful in isolating, cloning and utilizing genes other than the RB gene and have application to other cancer suppressing genes as well. Following are more detailed explanations of each state of the process discussed above together with detailed examples of utilization of the RB gene.

B. INITIAL STEP OF IDENTIFYING CANCER SUPPRESSING GENES

In order to identify and clone cancer suppressing genes a known chromosome associated with a particular cancer is identified. In general, the chromosome carrying the defective cancer suppressing gene may be determined by examination of phenotypic expression in the absence of the chromosome. Further, such examination can be performed after a portion of the suspected chromosome has been altered by chemical or other techniques or by excision of portions of it. In general, understanding of the control of genetic expression has been based largely on the introduction of genes or other defined segments of DNA into cells and the assessment of the genes' ability to function normally.

Once a chromosome is selected, the locus is selected on the chromosome for the cancer suppressing gene to be determined. This is accomplished, for example, by the use of probes inserted at random at suspected location of the chromosome in order to establish the location of the gene. This technique is limited because of the large number of genes associated with a typical eukaryotic cell chromosome.

Secondly, the chromosomal DNA containing the suspected gene may be cut into fragments, for example, by mechanical excision, or by use of suitable restriction enzymes, or other means. This technique may be employed to establish gene location by, once again, ultimately evaluating the phenotypic expression of the DNA fragments.

Thirdly, a preferred method of identifying the location of the cancer suppressing gene is through the utilization of a marker gene. Ideally, the marker gene is located in close proximity to the locus of the cancer suppressing gene and, in addition, the marker gene is a readily observable phenotypic expression. Once the marker gene has been identified, chromosomal walking techniques are employed in order to analyze portions of the chromosomal DNA in order to locate the cancer suppressing gene. Chromosomal walking depends on isolating a small segment of DNA from one end of a first recombinant and using this piece of DNA as a probe to rescreen the phage or cosmit library in order to obtain a recombinant containing that piece of DNA and the net portion of the genome.

The second recombinant is then used to obtain a third, and so in, to yield a set of overlapping cloned segments. In general, the chromosome walking technique may be utilized bidirectionally along the chromosome, starting with the marker gene.

B1. IDENTIFICATION OF THE MARKER GENE

An actual example of the use of a marker gene was the identification, purification and cloning of the esterase D gene. Chromosome mapping of the esterase D gene to the chromosome 13q14.11 region was accomplished by correlating loss of the esterase D gene activity with known deletions on chromosome 13 of mutant cells.

Since it was known that the esterase D gene was located in close proximity to the RB gene, it was used as a starting point for identifying the RB gene by chromosomal walking. Because of its proximity to the RB gene, the esterase D gene was ideal as a marker gene. Not only did its proximity reduce the chromosomal walking necessary to locate the cancer suppressing gene, genetic alterations of the esterase D gene would result in, not only an altered esterase D gene phenotype but, in addition, an altered cancer suppressing gene phenotype.

In the development of the marker gene, the amino acid sequence of human esterase D enzyme was identified as was the nucleotide sequence of esterase D cDNA. The chromosomal location of the gene was located and cloned esterase D cDNA was utilized as a genetic marker.

The use of the marker, as a starting point for chromosomal walking and the further use of the esterase D cDNA as a probe resulted in the location and cloning of the retinoblastoma gene.

While the following summarizes the utilization of human esterase D cDNA as a genetic marker, for a complete disclosure of the method, reference may be made to pending patent application Ser. No. 091,547.

Esterases belong to the family of nonspecific enzymes that catalyze the hydrolysis of esters. Human esterase D (ESD) is one member of the esterase family distinguishable by its electrophoretic mobility and its relative specificity for methylumbelliferyl esters as substrate. Human ESD is a dimeric enzyme in that it displays several phenotypes as a result of the expression of codominant autosomal alleles, primarily allele ESD 1 and ESD 2. The polymorphic nature of human ESD has been of value in the use of human ESD as a marker in studies of population genetics *Nature,* 304:451–453 (1983); and *Am. Hum. Genet.,* 39:1–20 (1975).

The activity of ESD enzyme depends on the normal function of the ESD gene. Consequently, absence, complete or partial inactivation, deletion of one ESD allele, mutation or other alterations in ESD sequences will result in decreasing ESD activity. For example, the tissues of individuals with a deletion of one chromosome 13 show only 50% of the ESD activity of that found in the healthy individuals possessing a normal set of two chromosomes 13, *Science,* 219:973–975 (1983).

The genetic locus of ESD was mapped to the chromosome 13q14:11 region by correlating the loss of enzyme activity with deletions of chromosome 13, *Science,* 208:1042–1044 (1980). The regional assignment of ESD to 13q14:11 region coincides with the location of the retinoblastoma (RB) gene, shown to be involved in the tumorigenesis of retinoblastoma, *Am. J. Dis. Child.,* 132:161–163 (1978); *Science,* 219:971–973; *Science,* 213:1501–1503 (1981). The development of homozygosity or hemizygosity in the 13q14 region by deletion, mitotic recombination, or chromosomal loss has been interpreted as a primary event in retinoblastoma. This finding is consistent with the hypothesis that inactivation of both alleles of a gene located at 13q14:11 is required for tumorigenesis.

By examining levels of esterase D mapping to the 13q14.11 region, it was previously inferred that one chromosome 13 in the somatic cells of the retinoblastoma patient contained a submicroscopic deletion of the RB and esterase D loci and that this chromosome was retained in the tumor, while the normal chromosome 13 was lost, *Cancer Gen. Cytogen,* 6:213–221 (1983).

The localization of the ESD and RB genes in the same chromosomal region provides an advantageous approach for evaluation of the RB gene functioning, for discovery of RB chromosomal patterns, for cloning of the RB gene, for isolation of the RB gene and for identifying the RB gene sequence by chromosomal walking, using ESD as the starting point *Science.* 235:1394–1399 (1987). The tight linkage between these two genes allows the ESD gene to serve as a crucial marker in elucidating the behavior of the RB gene, *Science,* 219:973–975 (1982); and *Nature,* 304:451–453 (1983).

Other than the RB gene, the defective gene in Wilson's disease has been found to be located in the same chromosomal region, 13q14:11, and thus was found to be linked to the ESD gene, *Proc. Natl. Acad. Sci.,* 82:1819–1821 (1985). Wilson's disease, also known as hepatolenticular degeneration, is a hereditary disease of ceruloplasmin formation transmitted as an autosomal recessive. It is characterized by gross reduction in the incorporation of copper in ceruloplasmin resulting in decreased serum ceruloplasmin and copper values, and increased excretion of copper in the urine. The close linkage found between Wilson's disease locus and the ESD gene, which can serve as the polymorphic marker for Wilson's disease, has profound implications both for investigation of the primary gene defect and for clinical use.

The identified and cloned ESD cDNA thus would provide a valuable marker in the identification and sequencing of both the RB gene and the Wilson's disease gene would lead, eventually, to diagnosis and treatment of these disease.

In the pending U.S. patent application Ser. No. 091,547, a process was disclosed for purifying human ESD by first obtaining the human ESD from human tissue, lysing said tissue, extracting the lysed tissue with an organic solvent, partially purifying the extract and then separating the purified ESD by column chromatography.

The purified human ESD obtained was subsequently used in the preparation of specific rabbit anti-esterase antibody.

The antibody was utilized to identify and isolate ESD cDNA clones through a technique for cloning genes by using specific antibody as probes and for isolating unknown proteins encoded by cloned DNA. In general, the method used an expression vector λgt11 (lac5 nin5 cI857 S 100__ that permitted insertion of foreign DNA into β-galactosidase structural gene lac Z and promoted synthesis of hybrid fusion proteins, DNA, 3:437–447 (1984).

B2. MAPPING OF THE ESD GENE

Chromosome mapping of the ESD gene to the chromosome 13q14.11 region was accomplished by correlating loss of the ESD enzyme activity with known deletions on chromosome 13 of various mutant cells. In addition, analysis supported the conclusion that the EL22 clone containing the esterase D gene was mapped to the chromosome 13q14 region.

Using the esterase D cDNA as probe, it was found that (i) the size of the esterase D mRNA is 1.3–1.4 kb; (ii) the gene is around 20–35 kb, indicating the presence of large introns scattered over this genome; and (iii) the esterase D gene is indeed located at 30 chromosome 13q14 region. Also, the deduced amino acid of the esterase D gene was unique when compared to 4000 other well-characterized proteins.

The above mapping data shows that the ESD gene is located at chromosome 13q14.11 region with no meiotic recombination observed with the RB gene. These findings indicate that both genes are in close proximity although the exact kilobase-pair distance between them is unknown. Normally, the maximal DNA content of a band, such as q14:11 does not exceed, on the average, 1000 kb. On the other hand, the distance between the RB gene and the ESD gene may be just a few kilobases.

Based on the lack of esterase D activity in LA-RB 69 retinoblastoma cells, it has been suggested that a submicroscopic deletion had occurred in the tumor cells resulting in the loss of both the RB and the esterase D genes. It was believed that some abnormality, perhaps in the regulatory region, must occur to cause a substantial reduction in the expression of the esterase D gene and diminution of the enzyme activity. It was plausible to expect that this abnormality would be likely to interfere with the RB gene expression leading to tumorigenesis.

B3. CLONING THE ESTERASE D GENE

Since the genetic locus involved in the genesis of retinoblastoma is tightly linked to the esterase D gene, it was crucial to clone the esterase D gene. The availability of the completely sequenced cDNA clone and ESD gene facilitated retinoblastoma studies in that it allowed the identification of the RB gene, its cloning and sequencing, and thus enabled a clinical diagnosis of retinoblastoma and genetic corrections.

Recently, the human esterase D was successfully purified. The polyclonial anti-esterase D antibody was prepared, and oligonucleotide probes complementary to certain ESD polypeptides were constructed. The complete amino acid sequence of ESD protein was determined, and ESD cDNA was cloned. The complete nucleotide sequence of both ESD cDNA and the ESD gene were identified and the ESD gene was localized.

In addition, specific human anti-esterase D antibody was able to bind a polypeptide with a molecular mass of about 33–34 kDa subsequently identified as ESD.

Using this anti-esterase D antibody, a protein corresponding to human esterase D was immunoprecipitated from mouse, rat, hamster, and monkey cells.

The above described immunologic reaction was then used in identification and the isolation of the ESD cDNA clones from two Agt11 cDNA libraries. The technique of cloning genes by using specific antibody as probes and for isolating unknown proteins encoded by cloned DNA is well known. In general, the method uses an expression vector, λgt11 (lac5 nin5 cI857 S 100) that permits insertion of foreign DNA into B-galactosidase structural gene lac Z and promotes synthesis of hybrid fusion proteins, *DNA*, 3:437–447 (1984).

It was presumed that since ESD was shown to be present in many bodily tissues, the mRNA coding for ESD would be readily present in tissue extracts and/or in certain tissue tumors. Human hepatoma and human placenta tumors both have a relatively high level of expression of ESD mRNA and were, therefore, particularly suitable for the detection of specific ESD cDNA clones in the library. Therefore, these two tumors were chosen for construction of the ESD cDNA libraries in λgt11 vector.

Following immunoscreening of these libraries with anti-esterase D antibody, four clones were obtained. Two of the clones, with identical 1.1 kb (1100 bp) inserts, were called EL22a and EL22b. After analysis it was concluded that the EL22 clone is, in fact, the esterase D cDNA.

To determine the size of ESD mRNA, RNA blotting analysis was performed and the size of mRNA of two cell lines was found to be ≈14,5S(1.3–1.4 kb).

A distribution of the ESD gene in the human genome was determined by Southern genomic blotting analysis using $^{32}$P-labeled EL22 clone. It was found that the esterase D gene was distributed over 20–40 kb in the human genome. The combined size of the DNA fragments with positive hybridization was 20–40 kb, indicated that there are large intron sequences in the ESD genome. This was subsequently confirmed by characterizing the complete genomic esterase D clone.

C. GENETICS OF ONCOGENICITY AND CLONING OF CANCER SUPPRESSING GENE

After identifying and cloning the marker gene, its associated cancer suppressing gene is then identified and cloned. Chromosomal walking techniques are utilized to locate the cancer suppressing gene to be found. While the examples herein disclosed relate to use of the esterase D gene as a marker and of the evaluation of the RB gene in oncogenicity, it is understood that the examples disclosed herein will equally apply to the marker genes and the respective cancer suppressing genes as breast cancer suppressing genes, Wilm's tumor suppressing genes, Beckwith-Wiedemann syndrome suppressing gene, bladder transitional cell carcinoma suppressing gene, neuroblastoma suppressing gene, small cell lung carcinoma suppressing gene, renal cell carcinoma suppressing gene, acoustic neuroma suppressing gene, colorectal carcinoma suppressing gene, and others.

The chromosome walking technique performed as previously described can be utilized for location identification, purification and cloning of the above cancer suppressing genes. In general, analysis of the cancer suppressing gene activity can be determined by observation of the gen's phenotypic expression.

C1. GENETICS OF RETINOBLASTOMA

As an example of the practice of the present invention, the RB gene role in suppressing retinoblastoma has been determined.

The genetic control of retinoblastoma and suppression of carcinogenicity were evaluated by means of the cloning, isolation, identification and sequencing of the retinoblastoma gene. The cloned retinoblastoma gene cDNA was prepared and used as a tool for diagnosing retinoblastoma, osteosarcoma and fibrosarcoma. Development of the retinoblastoma gene led to the therapeutic application whereby a defective gene in cancer cells may be replaced with a normal gene thereby suppressing cancer formation.

While the following summarizes the method of development of the retinoblastoma gene, for a complete disclosure, reference may be made to pending patent application Ser. No. 108,748.

It is increasingly evident that carcinogenesis is associated with genetic alterations in tumor cells. Some of these alterations may occur in precursor somatic cells during the life of an individual, while other mutations might be inherited from a parental germline. The latter type of inheritance would explain cases of familial cancer and inherited cancer predisposition. Cancers with known familial occurrence include retinoblastoma, nephroblastoma (Wilm's tumor), neuroblastoma, osteosarcoma, renal cell carcinoma, melanoma, and breast cancer.

Several approaches have been applied to identify genetic elements involved in tumorigenesis. oncogenes were initially defined in tumor-inducing retroviruses and tumor DNA capable of transforming non-neoplastic cells in culture. Most oncogenes are activated homologues of protooncogenes that exist in normal cells.

Another class of cancer genes has been proposed for which loss of gene function is associated with oncogenesis. The existence of such genes was first indirectly suggested by studies with restriction fragment length polymorphisms (RFLPS) that indicated a loss of specific chromosomal regions in tumor DNA compared to somatic DNA from the same patients. The "loss of heterozygosity" has been observed in many tumor types including retinoblastoma, osteosarcoma, Wilm's tumor, hepatoblastoma and rhabdomyosarcoma.

Genes giving rise to tumors by loss of function have been termed "recessive oncogenes" or "cancer suppressing genes" since the presence of one or more normal alleles in a cell is apparently sufficient to prevent expression of the cancer phenotype.

Retinoblastoma is an intraocular cancer of early childhood that arises from the developing retina. It has been reported that its incidence is about 1 in 20,000 live births and it is the most common intraocular tumor of the pediatric age group. Two forms of retinoblastoma are distinguished on a genetic basis. The hereditary form is an autosomal-dominant cancer susceptibility trait: each offspring of a carrier parent has a 50% chance of inheriting the trait, and 90% of carriers will develop retinoblastoma. Multiple or bilateral retinal tumors are indicative of, and typical for, hereditary retinoblastoma. Furthermore, carriers are at high risk of developing additional primary neoplasms later in life; these second cancers are of otherwise unusual types, such as osteosarcoma or fibrosarcoma, and are usually fatal. In contrast, patients with nonhereditary retinoblastoma have single, unilateral retinal tumors and no increased risk of second cancers. However, some of the patients with unilateral retinoblastoma actually have the hereditary form. Because of its clear-cut inheritability, retinoblastoma has been a prototypic model for the study of genetic determination in cancer.

It has been inferred that retinoblastoma could result from as few as two "hits", or mutational events and it has been hypothesized that two hits served to inactivate both alleles of a singe gene (RB) that essentially functioned to suppress retinoblastoma formation. An individual inheriting a mutant RB allele in all somatic cells would be predisposed to getting retinoblastoma by an additional mutation of the other RB allele in one precursor cell (retinoblast). In sporadic cases, both RB alleles would have to be inactivated by two independent somatic mutations in a single retinoblast. This model could explain both the earlier onset and multiplicity of tumors in predisposed individuals. However, the validity of this hypothesis remains to be demonstrated at the molecular level.

Karyotypic examination of somatic cells (fibroblasts) from patients with hereditary retinoblastoma disclosed a minor subset of cases containing visible deletions of the long arm of chromosome 13. Similar deletions were also identified in retinoblastoma tumor cells. Studies of a large retinoblastoma pedigree show that normal individuals carried a balanced translocation involving 13q14, while those with retinoblastoma had only one l3q14 region. Band 13q14 was common among all deletions and presumably contained a gent (RB) determining susceptibility to hereditary retinoblastoma; these deletions also removed one allele of the gene for a polymorphic marker enzyme, esterase D.

It is known that the RB gene has a regulatory function and that its presence and normal function prevent the development of the retinoblastoma. On the other hand, absence, malfunctioning or inactivation of the RB gene causes the development of, or genetical predisposition and susceptibility to, the retinoblastoma and is believed to be the primary cause for both hereditary and acquired retinoblastoma, and for the secondary malignancies often recurring in retinoblastoma patients such as osteosarcoma, and fibrosarcoma.

Therefore, it is useful to determine if a genetic predisposition exists in a fetus or if there is a susceptibility for acquiring retinoblastoma at a later age so that early diagnosis and possible treatment though genetic manipulation could be accomplished.

C2. MOLECULAR CLONING OF GENES FROM CHROMOSOME REGION 13q14

Since nothing was known a priori about the RB gene product, candidate genes were to be identified solely on the basis of appropriate chromosomal location and presumed "recessive" behavior. That is, an intact RB gene should be expressed in normal retinal tissue but not in retinoblastomas. "Reverse genetic" cloning strategies require a collection of one or more DNA probes from the region of interest. These may consist of probes for other known genes; or of anonymous DNA probes isolated at random by a number of techniques. Before attempting to clone the RB gene, several laboratories made major efforts to obtain probes for region 13q14. The polymorphic marker enzyme esterase D was mapped to 13q14 and is closely linked to the RB gene with no known recombinants. By generating specific antisera and partially sequencing the protein, esterase D cDNA fragments have been identified. Also available were anonymous DNA probes mapping to 13q14, such as H3-8, H2-42 and 7D2 that were isolated by random selection from chromosome 13-specific libraries.

After identification of the RB gene its cDNA sequence and genomic organization were determined. Pending U.S. patent application Ser. No. 098,612 discloses the amino acid sequence of a phosphoprotein located in the cell nucleus and having DNA binding activity.

C3. IDENTIFICATION AND ROLE OF THE RB GENE BY CHROMOSOMAL WALKING

The esterase D gene has been located, identified, sequenced and cloned. Further, it has been located in close vicinity to the RB gene. Therefore, it is useful as the starting point for identifying the RB gene by chromosomal walking. DNA fragments isolated from this process can then be used as probes to examine qualitative or quantitative differences in mRNA from fetal retinal cells and retinoblastoma cells. Detection of such differences would provide evidence that somatic mutations occur in the RB gene of tumor cells. The DNA fragments corresponding to the defective mRNA are the best candidates for the RB gene. Moreover, the availability of mutant cells with known deletion in 13q13.1–14.11 and 13q14.11–q22, respectively, enables determination of the correct direction of walking toward the RB gene.

Specific esterase D clone EL22 together with another probe H3-8 were mapped to the same chromosome region 13q14 as the known location of the RB gene.

Bidirectional chromosomal walking along the chromosome 13 DNA was instituted using esterase D and H3-d as probes to clone additional genomic DNA and cDNA. This alternative screening led to the identification of several distinct clones such as SD-1, SD-2, RB-1, RB-2 and RB-5.

Candidate RB genes were used as probes in RNA blotting to detect mRNA transcripts and clones RB-1 and RB-5 were hybridized with a 4.6 kb mRNA fragment obtained from the normal retinal and placental tissues. Hybridization under the same conditions with mRNA obtained from the retinoblastoma RNA transcripts was not observed at all.

Other types of tumors not related to retinoblastoma, namely neuroblastoma and medulloblastoma, displayed normal 4.6 kb mRNA transcripts.

Two cDNA libraries, placental and fetal retina, were rescreened with clone RB-1 for complete cDNA clone and resulted in the isolating of clone RB-5.

Additionally, more than 20 phage clones were isolated from a human genomic DNA library with RB-1 and RB-5 as probes and were subsequently characterized by restriction mapping and hybridization to subfragment cDNA probes. A restriction map of the RB gene was then constructed showing that the RB gene consists of at least 12 exons scattered over more than 100 kb of DNA.

Sequence analysis was performed and yielded the reconstructed complete DNA sequence. Deletion templates were generated which yielded greater than 95% of the sequence.

The sequence of the RB gene protein products was then predicted and an amino acid hydropathy plot constructed.

Through the method disclosed in pending patent application Ser. No. 108,748, a gene encoding a messenger RNA (mRNA) of 4.6 kilobases (kb), located in the proximity of esterase D, was identified as the retinoblastoma susceptibility gene on the basis of chromosomal location, homozygous deletion, and tumor-specific alterations in expression. Transcription of this gene was abnormal in six of six retinoblastomas examined. In contrast, full-length RB mRNA was present, in human fetal retina and placenta tumors, and in other tumors such as neuroblastoma and medulloblastoma. DNA from retinoblastoma cells had a homozygous gene deletion in one case and hemizygous deletion in another case, while the remainder were not grossly different from normal human control DNA.

The RB gene contains 27 exons distributed in a region of over 200 kb. Sequence analysis of complementary DNA clones yielded a single long open reading frame that could encode a hypothetical protein of 928 amino acids.

A computer assisted search of a protein sequence database revealed no closely related proteins. Features of the predicted amino acid sequence included potential metal-binding domains similar to those found in nucleic acid-binding proteins. These results suggested involvement of the RB gene as a recessive genetic mechanism for regulation of human cancers.

As indicated above, the initial starting point was the gene encoding esterase D which is linked to the retinoblastoma susceptibility locus in band 13q14.11 within an estimated 1500 kilobase range. The esterase D cDNA clone EL-22 was used as a probe to isolate its genomic DNA clones. Distal DNA segments of these genomic clones were used to isolate additional genomic clones. At 20 kb intervals in walking regions, unique sequences were identified that were used as probes to isolate cDNA clones from fetal retina and placenta libraries. A similar strategy using H3-8 as probes was performed to isolate the candidate genes. A bidirectional chromosome walk covering hundreds of kb has been established by alternately screening genomic and cDNA libraries.

Candidate RB genes were used as probes in RNA blotting analysis to detect relevant messenger RNA (mRNA) transcripts polyadenylated RNA was prepared from human fetal retinas (obtained by dissection of about 25 first- or second-transfer fetal eyes) and from portions of normal human placentas. Since the primary retinoblastoma tumor samples large enough to yield sufficient mRNA for analysis are not usually available, polyadenylated RNA was isolated from cultured cells of six retinoblastomas. Additionally, polyadenylated RNA was isolated from three neuroblastomas and one medulloblastoma and from a primary medulloblastoma specimen.

Esterase D transcripts (1.4 kb) were detected in all tumor and tissue samples. This finding was consistent with the known "constitutive" expression of esterase D. Esterase D hybridization was subsequently used as a positive control.

Thus, only gross deletions but no small partial deletions of the RB gene were seen in these tumors, and detection of an intact genome did not imply normal gene expression. Such a disparity may be due to mutations in the promotor region. Explanations for decreased mRNA transcript size include small deletions within exons (which might not sufficiently alter gel mobility of large exon splicing sequences or other mRNA processing signals.

The numerous large Hind III bands seen on DNA blotting analysis suggested that the RB locus was spread over a rather large genomic region. To further clarify genomic structure, more than 20 phage clones were isolated from the human genomic DNA library with RB-1 and RB-5 as probes. These clones were characterized by restriction mapping and hybridization to subfragment cDNA probes. In conjunction with data from genomic DNA blotting, the Hind III restriction map of the RB gene was constructed. The RB gene consists of 27 exons scattered over more than 200 kb of DNA. One large intron of at least 50 kb is located between exons from the RB-1/RB-5 overlap region.

Recently described, Nature, 323:643–646 (1986) was a cDNA clone with properties that were attributed to the RB gene. This clone detected a 4.7-kb mRNA transcript present in adenovirus 12-transformed retinal cells but absent in four of four retinoblastoma cell lines. Deletions involving part or all of this gene were observed in five retinoblastomas, but none of these were internal homozygous deletions. These findings were not sufficient to precisely identify the RB gene. Sequence data were not included in the report, the restriction map of the cDNA clone was similar to those found in this invention.

As noted above, the RB gene expression, while specifically altered in retinoblastoma, was not confined to normal fetal retina but was also seen in at least one other normal unrelated tissue, placenta. For a more extensive survey, mRNA from fetal and adult rat tissues were prepared and analyzed by RNA blotting. A 4.6-kb mRNA transcript (presumably the normal size for rat) was detected in all tissues, though quantity varied markedly. A second species of transcript, approximately 2.3 kb in size, was apparent in fetal rat brain. This short transcript may represent either differential processing of the RB gene or transcription of a separate but closely related gene.

Recently another RB cDNA clone was isolated that contained an additional 234 base pairs on the 5' end. The revised RB cDNA sequence had an additional methionine codon at nucleotide 139. When this methionine was used as initiation codon, the predicted RB protein had 928 amino acids and a molecular weight of 110 kD. The second in-frame methionine was at base 346. Since the nucleotide sequence at the first ATG is not typical of other known mRNAs, the start codon assignment should be regarded as tentative. Later, the in vitro translation results favored the first methionine as the authentic initiation site. A computer search of the National Biological Research Foundation protein sequence database sequence detected no strong homology with any of more than 4000 published amino acid sequences. However, a number of nucleic acid-binding proteins and viral proteins showed weak sequence homology, with a yeast DNA-directed RNA polymerase having the highest homology score.

The predicted protein sequence included ten potential glycosylation sites but a candidate transmembrane domain (at least 20 consecutive hydrophobic residues) was not found. The amino acid hydropathy plot showed a mildly hydrophobic region near the putative amino terminus and a hydrophilic region at the carboxyl terminus. Two pairs of short amino acid sequences that were bracketed by cysteine and histidine residues in the manner of metal-binding domains found in nucleic acid-binding proteins were identified. A region of 54 amino acids from position 663 20 to 716 contains 14 proline residues (26%). Such proline-rich regions have also been observed in nuclear oncogene proteins myc and myb. While the significance of these observations is not well established, they suggested that the RB gene product may be a nucleic acid-binding protein. Subsequently, the RB protein ppRB$^{110}$ as been found to be primarily located in the cell nucleus.

The retinoblastoma gene has been previously found to be of a recessive nature. Tumor-specific alterations in gene expression provide the best evidence for identifying this gene as RB, and the examples of homozygous deletion and absence of mRNA expression support its postulated recessive nature.

Hereditary retinoblastoma patients have a high incidence of osteosarcoma as a second primary cancer. Inactivation of the retinoblastoma susceptibility (RB) gene has been implicated in the genesis of osteosarcoma by chromosomal homozygosity of the 13q14 region found in several osteosarcoma patients with or without retinoblastoma history.

In view of the above, it is clear that the role of the RB gene in tumor formation is of more general interest than simply that attendant to a rare childhood cancer. First, recessive genes similar to RB may control other unusual embryonal childhood cancers such as nephroblastoma (Wilm's tumor), hepatoblastoma, embryonal rhabdomyosarcoma, and neuroblastoma. Like retinoblastoma, all of these tumors resemble massive overgrowth of tissues found in normal embryogenesis. Nephroblastoma has been associated with deletions of chromosome region 11p13, and adjacent polymorphic markers become homozygous in these tumors.

C4. THE RB GENE IN OTHER CANCERS

Since the sequence of the RB gene is now known, the role of the RB gene in other tumors may now be explored. Retinoblastoma patients have a high rate of second malignancies occurring at a variety of sites. Osteosarcoma is the most common. Reduction to homozygosity in region 13q14 has been reported in osteosarcomas even without prior retinoblastoma, which suggests a common oncogenic mechanism for the two tumors despite their histologic and oncologic dissimilarity. In contrast, neuroblastoma and medulloblastoma, which are considered closely related to retinoblastoma, apparently do not involve alterations of RB. Further study of the RB gene will likely provide insight into unifying mechanisms of oncogenesis.

By analogy to retinoblastoma, a class of "cancer suppressing genes" has been postulated to explain other types of inherited cancers, and tumor-specific chromosomal deletions. Retinoblastomas and osteosarcomas often occurred in the same patients, and several osteosarcomas (from patients both with and without retinoblastoma history) demonstrated a loss of heterozygosity of chromosome 13 markers. A few breast cancers also showed specific loss of chromosome 13 heterozygosity. Loss of heterozygosity has been found at chromosome 11p in Wilm's tumor (consistent with known deletions), tumors of the Beckwith-Wiedmann syndrome, transitional cell carcinoma of bladder, and, again, breast cancer. Similarly, other suppressing loci have been implicated in neuroblastoma, small cell lung carcinoma, renal cell carcinoma, acoustic neuroma, and colorectal carcinomas.

The RB gene was initially identified on the basis of altered RB gene expression in retinoblastoma tumors compared to that of normal tissues. Many additional tumors and neoplastic cell lines have been examined, and several with either DNA rearrangements, altered RB mRNA, or absent RB protein have been found. For example, of eight osteosarcoma cells lines tested, three (G292, SA0S2 and OHS) showed abnormalities at the protein level. G292 expressed RB protein of increased molecular mass, whereas SA0S2 and OHS completely lacked the RB protein. Both osteosarcoma cell lines without RB protein had shortened RB mRNA transcripts, and G292 had both shortened and normal-sized RB mRNA transcripts. Cell line SA0S2 had homozygous deletion of the 3' end of the RB gene, involving exon-containing Hind III fragments of exons in an internal 7.5 kb Hind III fragment. However, G292 had a grossly normal RB gene structure.

RB protein was also absent from one synovial sarcoma cell line (GHM) in which norma-sized RB mRNA was present. GHM DNA was also grossly normal by DNA blotting analysis with RB cDNA probes. This cell line constitutes the first known example of RB gene inactivation apparently solely at the protein level. A fresh specimen from a synovial sarcoma tumor, SDSY1, was also analyzed. Both normal-sized and lengthened RB mRNA transcripts (6.5 kb) were observed by RNA blotting and is apparent that normal-sized transcripts may be derived from non-neoplastic cells intermixed in whole tumors. Analysis of SDSY1 DNA with RB cDNA probes showed extra restriction fragments in addition to all normal fragments after digest with Hind III, EcoR I and Pst I endonucleases, suggesting internal RB gene duplication. Duplication of exons in these fragments would add approximately 1.1 kb to the RB mRNA transcript, and would substantially account for the observed mRNA size (6.5 kb). Other studies have confirmed the presence of RB gene mutations in fresh osteosarcomas and a variety of soft-tissue sarcomas from patients without a history of retinoblastoma.

Recently, RB gene inactivation in two of nine human breast cancer cell lines was found. The RB gene of one cell line had a homozygous internal duplication of 5 kilobase (kb) region containing exons 5 and 6. The RB mRNA transcript was correspondingly lengthened, and it was inferred that its translation was terminated prematurely due to a shifted reading frame. The other cell line had a homozygous deletion of the RB gene that removed the entire gene beyond exon 2. The RB gene product, pp110$^{RB}$, was not detectable in either cell line by immunoprecipitation with specific antibodies. Also reported recently was loss of RB gene expression in some cell lines derived from small cell carcinomas of the lung.

These results support a role for RB gene mutation in the genesis of cancers other than retinoblastoma. However, for each tumor type, mutations have been detected in only a fraction of cases. There are two possible explanations for this: 1) there is genetic heterogeneity among these tumors, such that only a fraction of each tumor type involves the RB gene; and/or 2) some inactivating mutations of the RB gene are not being detected.

C5. CLONING THE RB GENE

The identification, isolation, determination of the exact nucleotide sequence and cloning of the RB gene has a multiple utility.

The primary utility lies in the sequence transcription into its corresponding mRNA which is in turn translated into RB gene protein product. Protein product can then be used as an antigen in obtaining the specific anti-RB protein antibody. Antibody are then used as a diagnostic immunomarker for the investigation of the presence or absence os the RB gene protein in the examined tissue. If the RB protein is present, the RB gene is intact and retinoblastoma not present. If, on the other hand, the protein is absent or altered, the deficient RB gene is indicated and resulting retinoblastoma or other cancers or susceptibility thereto is indicated.

The sequence of the RB gene can be further utilized in producing the specific RB gene cDNA clones which can be used as the genetic markers and probes in isolation, identification and sequencing of other related genes or genes located in the proximity of the RB gene the function of which is as yet unknown.

The control and regulatory function of the RB gene is exerted through the RB protein which is instrumental in inhibiting other gene's oncogenic activity and restraining the malignant cell growth.

C6. ONCOGENICITY BY MUTANT RB GENES

The absence of antigenically detectable RB protein in retinoblastoma cells supports the notion that oncogenicity by mutant RB genes is achieved through complete loss of gene product function even in those cell lines containing shortened RB mRNAs.

The hypothetical protein predicted from the nucleotide sequence was expected to have MW about 106 kD. The immunoprecipitated protein has a MW about 110–114 kD. The complete RB protein amino acid sequence is illustrated in Table 1. This complete sequence obtained from the newly reconstructed clone which contains the most 5' end stretch missing in the original cDNA clone *Science,* 235:1394–1399 (1987).

TABLE 1

```
                      M  P  P  K  T  P  R  K  T  A  A  T  A  A  A  A  A  A  E  P  P  A  P  P  P  P  P  P  P  E  E  D  P  E   (34)
Q  D  S  G  P  E  D  L  P  L  V  R  L  E  F  E  E  T  E  E  P  D  F  T  A  L  C  Q  K  L  K  I  P  D  H  V  R  E  R  A   (74)
W  L  T  W  E  K  V  S  S  V  D  G  V  L  G  G  Y  I  Q  K  K  K  E  L  W  G  I  C  I  F  I  A  A  V  D  L  D  E  M  S   (114)
F  T  F  T  E  L  Q  K  H  I  E  I  S  V  H  K  F  F  H  L  L  K  E  I  D  T  S  T  K  V  D  N  A  H  S  R  L  L  K  K   (154)
Y  D  V  L  F  A  L  F  S  K  L  E  R  T  C  E  L  I  Y  L  T  Q  P  S  S  S  I  S  T  E  I  N  S  A  L  V  L  K  V  S   (194)
W  I  T  F  L  L  A  K  G  E  V  L  Q  M  E  D  D  L  V  I  S  F  Q  L  N  L  C  V  L  D  Y  F  I  K  L  S  P  P  H  L   (234)
L  K  E  P  Y  K  T  A  V  I  P  I  N  G  S  P  R  T  P  R  R  G  Q  M  R  S  A  R  I  A  K  Q  L  E  N  D  T  R  I  I   (274)
E  V  L  C  K  E  H  E  C  N  I  D  E  V  K  N  V  Y  F  K  N  F  I  P  F  H  N  S  L  G  L  V  T  S  N  G  L  P  E  V   (314)
E  N  L  S  K  R  Y  E  E  I  Y  L  K  N  K  D  L  D  A  R  L  F  L  D  H  D  K  T  L  Q  T  D  S  I  D  S  F  E  T  Q   (354)
R  T  P  R  K  S  N  L  D  E  E  V  N  V  I  P  P  H  T  P  V  R  T  V  M  N  T  I  Q  Q  L  M  H  I  L  N  S  A  S  D   (394)
Q  P  S  E  N  L  I  S  Y  F  H  H  C  T  V  H  P  K  E  S  I  L  K  R  V  K  D  I  G  Y  I  F  K  E  K  F  A  K  A  V   (434)
G  Q  G  C  V  E  I  G  S  Q  R  Y  K  L  G  V  R  L  Y  Y  R  V  M  E  S  M  L  K  S  E  E  E  R  L  S  I  Q  N  F  S   (474)
K  L  L  N  D  N  I  F  H  M  S  L  L  A  C  A  L  E  V  V  M  A  T  Y  S  R  S  T  S  Q  N  L  D  S  G  T  D  L  S  F   (514)
P  W  I  L  N  V  L  N  L  K  A  F  D  F  Y  K  V  I  E  S  F  I  K  A  E  G  N  L  T  R  E  M  I  K  H  L  E  R  G  E   (554)
H  R  I  M  E  S  L  A  W  L  S  D  S  P  L  F  D  L  I  K  Q  S  K  D  R  E  G  P  T  D  H  L  E  S  A  C  P  L  N  L   (594)
P  L  Q  N  N  H  T  A  A  D  M  Y  L  S  P  V  R  S  P  K  K  K  G  S  T  T  R  V  N  S  T  A  N  A  E  T  Q  A  T  S   (634)
A  F  Q  T  Q  K  P  L  K  S  T  S  L  S  L  F  Y  K  K  V  Y  R  L  A  Y  L  R  L  N  T  L  C  E  R  L  L  S  E  H  P   (674)
E  L  E  H  I  I  W  T  L  F  Q  H  T  L  Q  N  E  Y  E  L  M  R  D  R  H  L  D  Q  I  M  M  C  S  M  Y  G  I  C  K  V   (714)
K  N  I  D  L  K  F  K  I  I  V  T  A  Y  K  D  L  P  H  A  V  Q  E  T  F  K  R  V  L  I  K  E  E  Y  D  S  I  I  V   (754)
F  Y  N  S  V  F  M  Q  R  L  K  T  N  I  L  Q  Y  A  S  T  R  P  P  T  L  S  P  I  P  H  I  P  R  S  P  Y  K  F  P  S   (794)
S  P  L  R  I  P  G  G  N  I  Y  I  S  P  L  K  S  P  Y  K  I  S  E  G  L  P  T  P  T  K  M  T  P  R  S  R  I  L  V  S   (834)
I  G  E  S  F  G  T  S  E  K  F  Q  K  I  N  Q  M  V  C  N  S  D  R  V  L  K  R  S  A  E  G  S  N  P  P  K  P  L  K  K   (874)
L  R  F  D  I  E  G  S  D  E  A  D  G  S  K  H  L  P  G  E  S  K  F  Q  Q  K  L  A  E  M  T  S  T  R  T  R  M  Q  K  Q   (914)
K  M  N  D  S  M  D  T  S  N  K  E  E  K                                                                                   (928)
```

Single-letter abbreviations for the amino acid residues are: A, Ala; C, Cys; D, Asp; E, Gly; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

The amino acid sequence (Table 1) is written in the abbreviation code recognized in the art. Single-letter abbreviations for the amino acid residues are: A=Alanine, C=Cysteine, D=Aspartic acid, E=Glutamic Acid, F=Phenylalanine, G=Glycine, H=Histidine, I=Isoleucine, K=Lysine, L=Leucine, M=Methionine, N=Asparagine, P=Proline, Q=Glutanine, R=Arginine, S=Serine, T=Threonine, V=Valine, W=Tryptophane and Y=Tyrosine.

RB cDNA sequence Science, 235:1394–1399 (1987) contained a long open reading frame from nucleotide 1 through 2688, which when translated from the first methionine codon yielded a hypothetical protein of 816 amino acids and molecular weight 98 kD. Recently another isolated RB cDNA clone contained an additional 234 base pairs on the 5'end. The revised RB cDNA sequence still maintained the same open reading frame as in the original clones, and an additional methionine codon was found at nucleotide 139. When this codon was used as an initiation codon, the predicted RB protein had 928 amino acids and a molecular weight of 110 kD—identical to the apparent M.W. determined by SDS-PAGE. The additional 5' sequence contains a GC-rich region that translates into an unusual cluster of alanine and proline residues.

Discrepancies between actual and apparent molecular weights on SDS-PAGE may be explained by secondary protein modifications. Several potential N-linked glycosylation sites are present in the predicted amino acid sequence. However, when LAN-1 cells were grown in medium supplemented with $^{14}$C-galatose or $^{3}$H-glucosamine, labeled RB protein was not detected despite prolonged autoradiography. In addition, digestion of $^{35}$S-labeled RB protein by Endoglycosidase H according to the method described in J. Bill. Chem., 250:8569–8579 (1975), did not result in a reduction of apparent molecular weight.

When the neuroblastoma cells LAN-1 were metabolically labeled with $^{32}$p-phosphoric acid and immunoprecipitated, the immunoprecipated protein ran as a single band with molecular weight identical to the $^{35}$S-labeled RB protein. The results show Lanes 2+3 showing a $^{35}$S-labeled band at 110–114 kD and Lane 5— $^{32}$P-labeled band at 110–114 kD. Lanes 1 ($^{35}$S) and 4 ($^{32}$P) are immunoprecipitated with preimmune rabbit IgG. When the aliquots of RB samples labeled with $^{35}$S-methionine were digested overnight with Endoglycosidase H, there was no detectable reduction of molecular weight 110–114 kD. The above findings support the belief that the retinoblastoma gene is a phosphoprotein of MW 110–114 kD. The phosphoprotein was therefore named ppRB$^{110}$.

D. DIAGNOSTIC PROCEDURES UTILIZING CANCER SUPPRESSING GENE PRODUCTS

After locating and cloning a desired cancer suppressing gene, the cloned gene can be used to obtain a gene product useful in diagnosing for cancer related to the cancer suppressing gene.

The technique includes initially developing a product which can react with the cancer suppressing gene product of a patient's tissue sample. In this regard, the reaction between the product is observed to determine the presence or absence of the normal phenotypical expression of the cancer suppressing gene of the tissue sample.

More specifically, using the cloned cancer suppressing gene, an antibody is developed. The antibody, which is specific for the cancer suppressing gene protein product, is used to react with the cancer suppressing gene protein product in a patient's tissue sample for determining whether or not the cancer suppressing gene is functioning properly. In a typical case, proper cancer suppressing gene function is demonstrated when an immunocomplex between the antibody and the cancer suppressing gene protein product is formed. Failure of the immunocomplex is indicative of defective, abnormal or absent cancer suppressing gene protein product. Thus, failure of the antibody to form an immunocomplex with the patient tissue sample substrate is indicative of a defective or absent cancer suppressing gene in the patient.

The specific antibody is produced, in general, by utilizing the normal cancer suppressing gene protein product as an antigen according to known techniques. Other conventional techniques may also be employed for producing the desired antibodies.

As a specific example of the technique herein disclosed, the protein product of the RB gene has been identified. According to the method disclosed in pending U.S. patent application Ser. No. 098,612, immunoprecipitation of the phosphoprotein was accomplished utilizing preimmune rabbit anti-sera and, as disclosed in said application, a protein with MW 110–114kD was immunoprecipitated with anti-ppRB$^{110}$ IgG.

D.1 DIAGNOSTIC PROCEDURES FOR DETERMINING CANCER PREDISPOSITION

Once the cancer suppressing gene is identified and cloned, the clone is useful diagnostically. In this regard, patients can be screened for their predisposition toward cancer, by observing the phenotypical expression of a cancer suppressing gene in a tissue sample taken from a patient.

D2. IDENTIFICATION AND CHARACTERIZATION OF THE RB PROTEIN

As a specific example relative to the retinoblastoma cancer suppressing gene, phosphoprotein product of the retinoblastoma susceptibility gene has been located primarily in the cell nucleus having DNA binding activity. Its amino acid sequence has been identified. The phosphoprotein, identified as ppRB$^{110}$ is utilized in diagnosing retinoblastoma and other cancers involving the retinoblastoma gene, and, to some extent, in the treatment of these cancers and in evaluating the oncogenicity of other genes.

While the identification of ppRB$^{110}$ is summarized herein, for a complete disclosure thereof, reference may be made to the foregoing identified pending patent application Ser. No. 098,612.

As stated in pending U.S. patent application Ser. No. 098,612, experimental evidence indicates that complete inactivation of the RB gene is required for tumor formation, and that a new mode of function exists for the RB gene as a suppressing of the cancer phenotype.

Since gene action is generally intermediated by its protein product, it appears that the RB gene protein product would have a gene-regulatory activity.

Therefore, obtaining the complete amino acid sequence of the RB gene protein product, specific anti-retinoblastoma protein antibody, its biochemical characterization, subcellular localization and its DNA binding activity, are of importance for further elucidation of the RB gene regulatory and oncogenic activity.

The amino acid sequence of a protein can be determined by the genetic code of the particular gene responsible for that particular protein. Therefore, in order to isolate the protein, to determine its exact amino acid sequence and to determine its physiological function in the body, it is necessary to isolate and localize the responsible gene, to clone it and to sequence the cDNA which are useful in identification of the gene's specific protein product.

Using the method of chromosomal walking from other chromosome 13 markers, retinoblastoma gene and encoding of the amino acid sequence was identified at 13 chromosome, 13 q14:11 region. By using esterase D cDNA clones and by screening the genomic and cDNA overlapping clones RB-1 and RB-2 of 1.6 kb, respectively, were identified in human cDNA libraries. Later on, another clone RB-5 was also identified.

First, the RB-1 clone was hybridized with 4.8 kb mRNA transcript in human fetal retina and placenta. In retinoblastoma samples, RB-1 clone either detected an abnormal mRNA transcript or the mRNA transcripts were not observed at all. Subsequently identified RB-5 clone, with a 3.5 kb insert, gave identical results as RB-1 in mRNA hybridization. Restriction enzyme analysis suggested that RB-5 and RB-1 clones overlapped in a 0.4 kb region and both together defined a DNA segment of about 4.6 kb, a size close to that of the normal RB mRNA transcript.

Nucleotide sequence analysis of clones RB-1 and RB-5 was performed by the dideoxy-terminator method described in *Proc. Natl. Acad. Sci.*, 74:5463–5467 (1977) and yielded the reconstructed complete cDNA sequence. Different deletion templates were generated by the "cyclone" method in single stranded M13 phage clones, which yielded greater than 95% of the sequence. The remaining gaps were sequenced by primer extension in both strands. The complete sequence identified in this way contained 4,523 nucleotides.

Further analyses supported the belief that the RB gene product was a nucleic acid-binding protein. In addition, nucleotide sequence analysis of RB cDNA clones demonstrated a long-open reading frame encoding a hypothetical protein with features suggestive of a DNA binding function. It was identified and used as an antigen for obtaining specific antibody and to determine its predicted DNA binding.

After preparing specific rabbit polyclonal antibody against RB protein, the purified anti-RB IgG antibody was used for immunoprecipitation, immunostaining and localization of RB protein. It was believed that the antibody will be useful for diagnostic identification of RB protein in human tissue samples.

To identify the RB protein, several human cell lines known to have either normal or altered RB expression were selected.

LAN-1 neuroblastoma cell line normal human fibroblasts, human hepatoma Alexander cell line and osteosarcoma U2OS cell line were used as positive controls containing normal RB mRNA. All these cells were obtained from the American Type Culture Collection (ATCC), Inc. depository. Cell lines with expected shortened or absent RB mRNA, such as retinoblastomas call lines Y79 (ATCC), RB355 (Gifted from Robert Philips, Toronto, Canada), WERI- 1, WERI-24, and WERI-27 (Gifted from T. Sery Wills' eye hospital, Philadelphia) were used as negative controls.

All normal human cell lines as described above and all cells from five retinoblastomas were labeled with $^{35}$S-methionine and immuniprecipitated with preimmune rabbit antibody IgG or rabbit anit-RB IgG.

Cells from all human cell lines were metabolically labeled with $^{35}$S-methionine according to procedure described in *J.*

Virol, 38:1064–1076 (1981). Labeled cell mixtures were immunoprecipitated with 1–20 ul, preferably 10 ul, of from 50 ug/ml–200 ug/ml, preferably 100 ug/ml of anti-RB antibody IgG using the procedure described in J. Virol, 38:1064–1076 (1981).

In all control cell lines a protein doublet with apparent molecular weight of 110–114 kD was detected. In retinoblastoma cell lines, or in cells immunoprecipitated with preimmune serum the protein doublet was not detected.

The RB proteins immunoprecipitated with rabbit anti-RB IgG were analyzed by SDS/polyacrylamide gel electrophoresis and auto-radiographed. The results indicated immunoprecipitation of the normal positive, i.e. RB protein containing cell lines labeled with $^{35}$S-methionine.

D2. LOCALIZATION AND FUNCTION OF ppRB$^{110}$

The cells from several vertebrate species, such as QT6 (quail), NIH/3T3 (mouse), Rat-2 (Rat) and cos (monkey) were labeled with $^{32}$P-phosphoric acid and proteins were immunoprecipitated with anti-RB IgG. Antigenically related proteins were detected in all cells with apparent similar molecular weights of 108 kD in quail, 120 kD in mouse, 128 kD in rat and 108–110 kD in monkey, as compared to 110–114 kD in human cells.

The predicted whole amino acid sequence of the ppRB$^{110}$ protein has several characteristics similar to those appearing in other oncogenes. Therefore, the subcellular localization of the ppRB$^{110}$ was investigated by cellular fractionization to identify the distribution of ppRB$^{110}$ among the nuclear, cytoplasmic, or cell membrane fractions.

It was determined that 85% of ppRB$^{110}$ was found in the nuclear fraction, while a small amount of the ppRB$^{110}$ was located in the cell membrane. There was no detectable presence in the cytoplasmic fraction.

To further substantiate that the ppRB$^{110}$ is localized primarily in the nucleus, the osteosarcoma cell lines U20S known to have an advantageous cell meorphology for immunohistochemical staining were used. As an experimental group, the U20S cells were immunoprecipitated with anti-ppRB$^{110}$ IgG. As a control group, the U20S cells were immunoprecipitated with preimmune IgG. Both groups were then incubated with rhodamine conjugated goat anti-rabbit IgG obtained commercially from Sigma. Immunofluorescence was observed in cells reacted with anti-ppRB$^{110}$ IgG, namely in the cell nucleus. Cells reacted with preimmune control did not show any fluorescence.

The subcellular localization of ppRB$^{110}$ in the nuclear fraction suggests that the RB protein plays an important regulatory function in regulating other genes and has a DNA binding activity.

Certain cell lines, particularly those from tumors others than retinoblastome, such as neuroblastome LAN-1 cells were radioactively labeled with $^{32}$P-phosphoric acid. Cellular lysates of these labeled cell mixtures were separated by single or double stranded calf thymus DNA-cellulose columns according to the method described in Mol. Cell. Biol., 6:4450–4457 (1986).

The results obtained suggest that the ppRB$^{110}$ binds only to a limited number of DNA sites that are easily saturated. It has been previously shown that other protooncogens such as c-myc, n-myc, c-myb and c-fos are nuclear phosphoproteins with DNA binding activity Mol. Cell. Bill., 6:4450–4457 (1986), Nature, 296:262–266 (1982). Oncogenic activation of these proto-oncogenes occurs by deregulation of gene expression or by structural modification, and the gene product is essential for oncogenicity.

While radioinmunoassay techniques were utilized, it is to be understood that the methods, such as enzyme immunoassay (Western blotting analysis), immunocytochemical assay, and others, are also suitable.

D4. REGULATORY FUNCTION OF ppRB$^{110}$

It is the ppRB$^{110}$ absence, and not its presence, that appears to be oncogenic due to the partial or complete inactivation of the RB gene. Therefore, the presence of the ppRB$^{110}$ somehow suppresses the oncogenic activity of other genes and disallows malignant cell growth. The ppRB$^{110}$ is thus an important regulatory protein which may prevent and inhibit, by its presence, and trigger, by its absence, the malignant growth. Thus, the importance of ppRB$^{110}$ is in regulating other genes. The absence or loss of ppRB$^{110}$ mediates oncogenicity.

D5. ppRB$^{110}$ AS A DIAGNOSTIC TOOL

The role of ppRB$^{110}$ as a mediator of oncogenicity leads to several practical applications.

First, the presence or absence of the ppRB$^{110}$ serves as a diagnostic tool in determination of the presence or predisposition to the retinoblastoma and other RB genes involved tumors of the animal fetus or embryo. Thus, early diagnosis allows an early warning and treatment of retinoblastoma and other tumors with the possibility of preventing development of secondary tumorigenesis.

In practice, the use of ppRB$^{110}$ to diagnose the presence or predisposition to retinoblastoma is through immunoscreening of the tissue biopsy with specific anti-ppRB$^{110}$ antibody. The bioptic tissue is either radioactively labeled and immunoscreened or the proteins extracted from bioptic tissue may be blotted on nitrocellulose filter and probed with labeled antibody according to methods known in the art as Western blotting.

It is expected that such readily available diagnostic methods will be used particularly for screening families with a history of hereditary retinoblastoma. Moreover, the diagnostic method is useful also for prediction of the development of secondary cancer, such as for example osteosarcoma, fibrosarcoma, glioblastoma, breast cancer, whether or not connected with retinoblastoma.

Another use is for tumorigenesis suppression where the absent ppRB$^{110}$ will be provided through molecular induction and gene transplanting of the RB cDNA to the individual in need of ppRB$^{110}$.

Still another application is the suppression of cancerogenous growth by providing the intact RB gene directly to the tumor cells. The cells in turn produce ppRB$^{110}$ which then effects the other tumorous cells.

E. GENE THERAPY AND PROHPYLAXIS

As previously described, diagnostic techniques, according to this invention, are useful in determining the susceptibility of individuals to cancer. However, in order to provide therapy and/or prophylaxis, the cloned cancer suppressing gene itself is delivered to the organism for controlling the suppression of cancer. The delivery of the cloned gene is achieved by conventional vectors, and in some applications, the cloned gene is appropriate for topical application.

The preferred delivery techniques include utilizing viruses liposomes, and other vectors. Delivery of cloned cancer suppressing genes, by means of suitable vectors, has prophylactic and/or therapeutic effects on patients having a defective or absent cancer suppressing gene while no adverse side effects would be experienced by the individual having the normal genetic complement. When a prophylactic situation is indicated, such as when a predisposition to cancer has been determined, for example by investigative diagnosis, cloned cancer suppressing genes are delivered to the patient. As indicated above, it is not expected that the administration of such cloned genes will adversely effect the individual with the ormal genetic complement.

As an example, the RB gene was tested therapeutically and prophylatically. Given the hypothetical cancer suppressing activity of the RB gene, an assay system for RB gene function was developed by introducing the gene into cultured tumor cells containing inactivated endogenous RB genes. Failure to find an effect in this simple assay would not necessarily invalidate the notion of genetic suppression of cancer. However, a positive result (suppression of the neoplastic phenotype) was realized to strongly reinforce this concept.

Direct detection of RB gene mutations would have clinical utility for the following reasons: 1) sporadic unilateral hereditary and nonhereditary cases could be distinguished by examining patients' fibroblasts, allowing accurate assessment of risk for second primary cancers and for transmission to offspring; 2) genetic diagnosis would be possible without informative RFLPs or without examining other family members. As described above, the intron 1 probe may be useful for this purpose depending on what fraction of mutant RB genes have rearrangements in this region. Other common sites of mutation in the RB gene might be identified, and probes designed specifically for their detection. It is possible that the RB gene promoter may be one such common site.

Antibodies to the RB protein may have diagnostic and/or prognostic application in clinical medicine. For example, mutations in the RB gene could be inferred by absence of immuniperoxidase staining of tumor sections, with nonneoplastic stroma providing an internal positive control. RB antibodies might be used to resolve anbiguities in tissue diagnosis of bone or soft-tissue neoplasms; Perhaps breast cancers could be usefully subclassified on the basis of RB gene involvement.

Finally, if inactivation of the RB gene is the primary cause of retinoblastoma and other cancers, then restoration of normal RB gene activity by gene transfer is a novel approach for future cancer therapy.

In order to test RB gene function at the cellular level, an assay system utilizing Rb and lux viruses was developed to introduce the gene into cultured tumor cells containing inactivated endogenous RB genes.

E1. PRODUCTION OF Rb AND LUX VIRUS INFECTION OF TUMOR CELL LINES

As an example of utilization of gene therapy, cloned RB genes were utilized in vivo and invitro studies. In this regard, cloned RB genes were introduced into tissue cultures. As another example, cloned RB genes were delivered prophylactically to one side of a nude mouse. Subsequently, carcinogens were introduced into both sides of the nude mouse. Tumor development was observed on one side while the side which had been prophylactically treated with cloned RB genes showed no tumor development.

Production of Rb and Lux viruses. Two different anphotropic retroviruses were constructed as shown in FIG. 1. One, Rb virus, consisted of MuLV LTRs (Moloney murine RB cDNA, and neo fused to the RSV (Rous sarcoma virus) promoter (LTR-RB-RSV-Nne-LTR) *Proc. Natl. Acad Sci.* 80:4709 (1983). Neo encodes Tn5 neomycin phosphotransferase that confers resistance to the neomycin analog G418, and was used to select against noninfected cells *J. Mol. Appl. Genet.* 1:327 (1982).

The other, Lux virus, was identical except that RB was replaced by the luciferase gene *Mol. Cell. Biol.* 7:725 (1987). The luciferase gene served not only as a control for specific effects of the RB gene, but also as a means to examine expression efficiency of the viral construct in different cells types. These two plasmids containing proviral DNA were then transfected into PA12 cells, which carry a packaging-deficient provirus and express all the necessary components for virus production including amphotropic envelope glycoproteins *Mol. Cell. Biol.* 5:431 (1985) (FIG. 1B).

Since this step produced very little infectious virus, supernatants harvested from transfected PA12 cells were used to infect the ecotropic helper line psi-2 *Cell* 33:153 (1983); ibid 37:1053 (1984). Individual G418-resistant colonies were isolated and screened for virus production and RB protein expression. Among 10 clones screened, eight produced $10^3$–$10^5$ G418-resistant cfu/ml when assayed with 208F rat fibroblasts as indicator cells.

Both parental clones and infected rat 208F cells expressed normal-sized human RB protein (110 kD) in addition to rodent RB protein (125 kD) when labeled with $^{32}$P-orthophosphate and immunoprecipitated with a polyclonal anti-RB antibody (anti-fRB) *Nature* 329:642 (1987). Finally, esotropic virus was used to infect PA12 cells, and a number of G418-resistant clones were screened for virus production and for expression of human RB protein. Five of clones expressed RB protein, the highest titer being $4\times10^4$ cfu/ml. Lux virus was obtained by an identical procedure except that colonies were screened for luciferase expression (FIG. 1B); the highest titer was $1\times10^5$ cfu/ml. These two viral stocks were used for all studies described below.

Infection of tumor cell lines; expression of RB Protein. Retinoblastoma cell line WERI-Rb27 and osteosarcoma cell line Saos-2 carry inactivated RB genes, as shown by the absence of normal RB protein *Nature* 329:642 (1987); J-Y Shew et al. unpublished. Both cell lines had partial deletions of the RB gene *Proc. Natl. Acad. Sci.* 85:2210 (1988); ibid 85:6017 (1988) and are referred to as RB-cells. Another osteosarcoma cell line, U-20S, expressed normal-sized RB protein and had apparently normal RB alleles *Nature* 329:642 (1987). These cell lines were used as recipients for infection by RB and Lux viruses. Due to the low titer and efficiency of infection by amphotropic retrovirus, all assays included selection with G418 to remove uninfected cells.

Figure 2A:
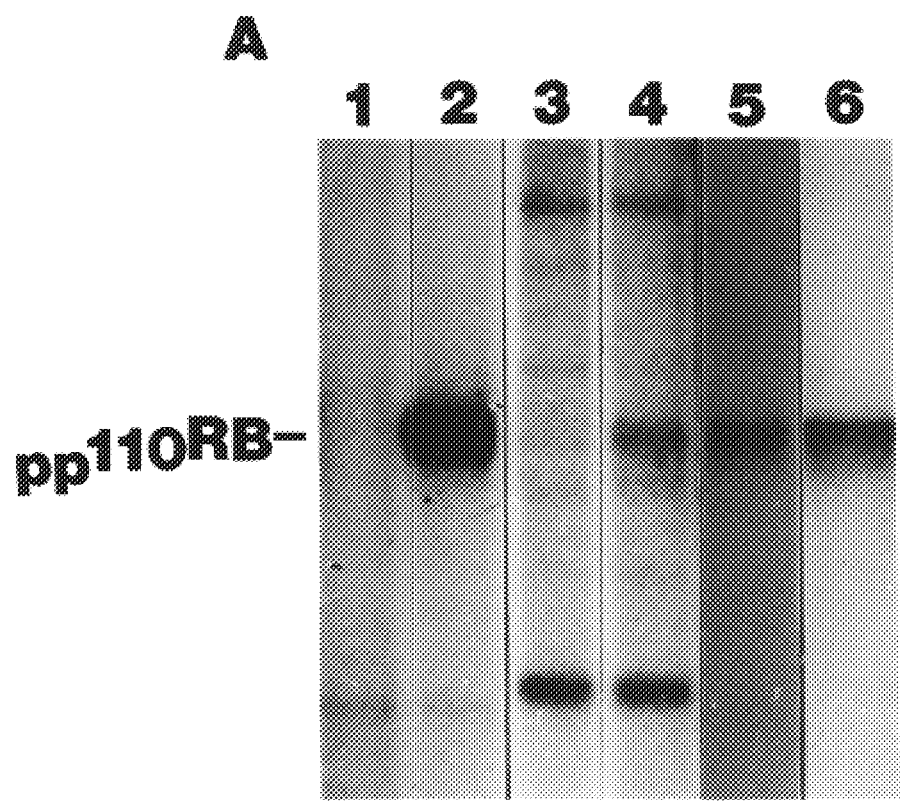
FIG. 2A is a chromatogram indicating the presence of normal-sized RB protein in cell lines after infection with RB virus and G418 selection.

After infection with RB virus and G418 selection, RB-cell lines expressed normal-sized RB protein when labeled with $^{32}$P-orthophosphate (FIG. 2A, lanes 2 & 4); Lux-infected RB-cells expressed no RB protein. As expected, RB protein expression in U-20S cells was not detectably altered after infection with Rb virus because of the presence of endogenous RB protein. However, G418 resistance of the selected clones indicated that viral infection had occurred.

To further verify the newly expressed RB protein in tumor cells, its cellular localization was examined. Most of the endogenous RB protein was localized to the nucleus in U-20S cells, as indicated by both cell fractionation and immunostaining. Rb virus-infected Saos-2 cells were immunostained using anti-fRB antibody. Nuclei were strongly positive for brown chromophore, reflecting RB protein location. Lux virus-infected cells were entirely unstained under the same conditions. Therefore the newly expressed RB protein was indistinguishable from native RB by three major biochemical indices (molecular weight, cellular localization and phosphorylation). RB gene expression in cells infected with Rb virus was monitored by immunoprecipitation with anti-fRB antibody before all subsequent experiments.

In order to establish that restoration of RB protein expression in RB cells influenced cell morphology and inhibited growth, the in vitro effects of RB gene expression were tested. Cultures of RB and Lux virus-infected tumor cells were compared after G418 selection as illustrated in FIG. 3. The morphology of U-20S cells, grown as a monolayer, was unchanged after infection with either virus. Monolayer culture of Saos-2 cells were unchanged by Lux virus infection, but showed obvious morphological alterations after Rb virus infection. Starting at two weeks post infection, two distinct cellular populations of G418-resistant cells were reproducibly observed. The majority of cells became flattened and greatly enlarged in average diameter (3–10 fold) compared to Lux virus-infected or uninfected cells (FIG. 3). The remaining cells were smaller and resembled uninfected parental cells. After four weeks in culture and further passaging, the larger cells were replaced by smaller cells that resembled parental or Lux virus-infected Saos-2 cells. Suspension cultures of WERI-Rb27 cells were also unchanged by Lux virus infection. Four weeks after Rb virus infection, however, moderately enlarged cells appeared that became increasingly numerous up to eight weeks. Large clumps of dead cells were also observed starting at six weeks (FIG. 3). After prolonged culture (<10 weeks), smaller cells that resembled parental or Lux virus-infected cells again became the predominat cell type.

Figure 4A:
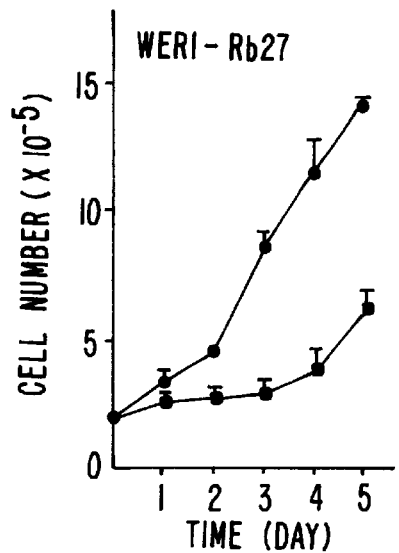
FIGS. 4A–C shows graphs of WERI-Rb27, Saos-2 and U-20S cell colony growth over a five day period.
Figure 4C:
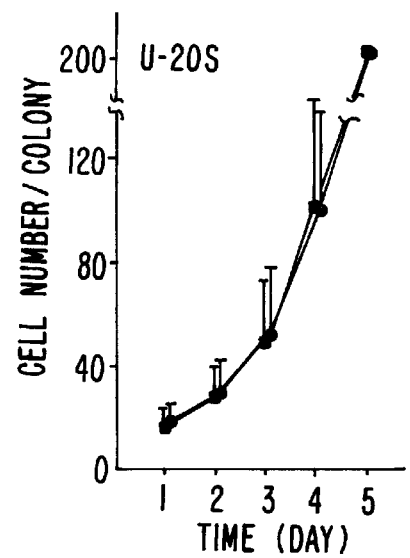
Figure 4B:
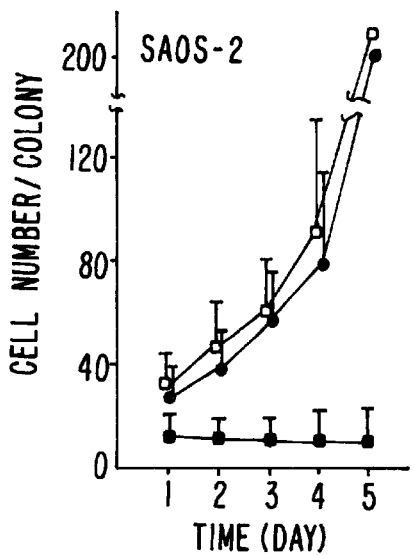

Variation in numbers of these morphologically distinct populations suggested that the two cell types differed in rates of cell division and/or longevity in culture. This difference was quantified for monolayer osteosarcoma cells using a colony growth assay. Infected Saos-2 and U-20S cells were plated at low density, and individual colonies formed by these cells were identified (FIG. 4). The number of cells in each colony, counted under a microscope, was followed over five days. With Saos-2 cells, the majority of colonies generated by Rb-virus infected cells either grew much more slowly than colonies of Lux virus-infected cells, or stopped growing completely after a few days (FIG. 4A). However, a few fast-growing colonies were always present. Colonies of U-20S cells infected with either virus did not differ in growth rate (FIG. 4B). Subpopulations of WERI-Rb27 cells could not be separately tracked because cells grew in suspension. However, bulk population growth of WERI-Rb27 cultures was noticeably slower after Rb virus infection. These results indicate that restoration of RB protein expression in RB-cells influenced cell morphology and inhibited growth.

Figure 5:
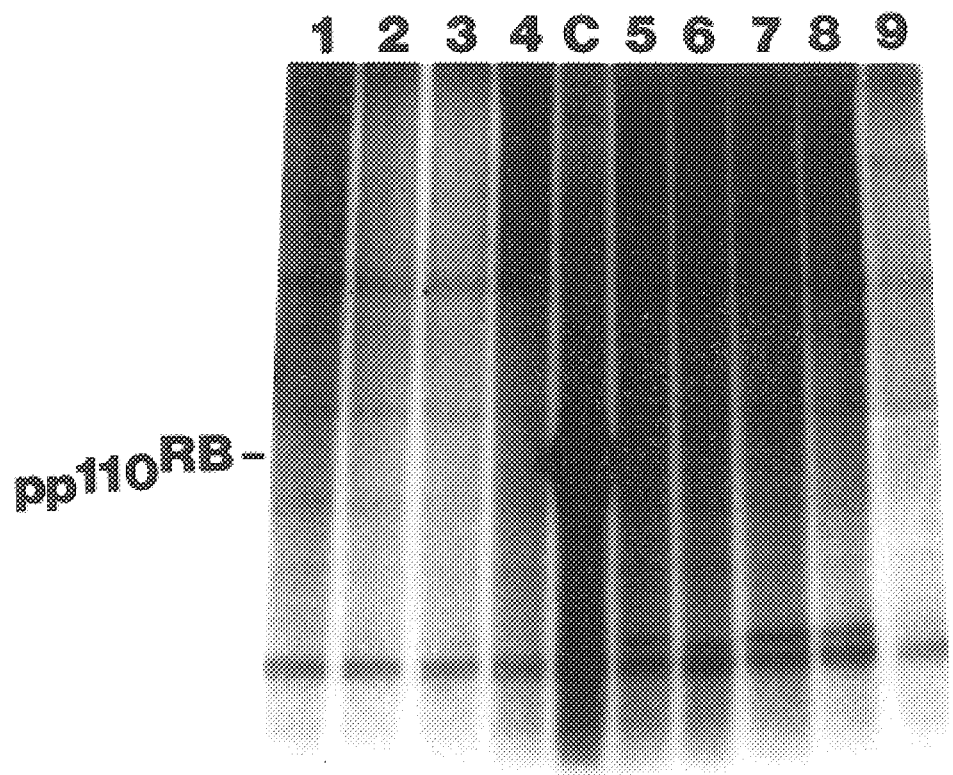
FIG. 5 is a chromatograph showing loss of RB protein expression in nine Saos-2 clones.

It was speculated that Rb virus-infected Saos-2 tumor cells that divided rapidly despite G418 selection were non-suppressed due to a defective viral RB gene. To test this proposal, fast-growing colonies of Saos-2 cells were cloned and grown into mass cultures, and expression of the RB protein was examined by immunoprecipitation. As shown in FIG. 5, nine of nine clones had completely lost RB protein expression despite continued G418 selection. Since Rb virus-infected Saos-2 cells in early culture expressed RB protein (FIG. 1), it was reasonably deduced that small, fast-growing cells did not contain RB protein. Inactivation of the proviral RB gene was not unexpected since native or recombinant retroviruses are prone to frequent mutations or epigenetic suppression of gene expression *Virol.* 46:939 (1971); *J. Virol.* 17:74 (1976); ibid 50:42 (1984); *Mol. Cell Biol.* 6:1141 (1986).

Figure 1B:
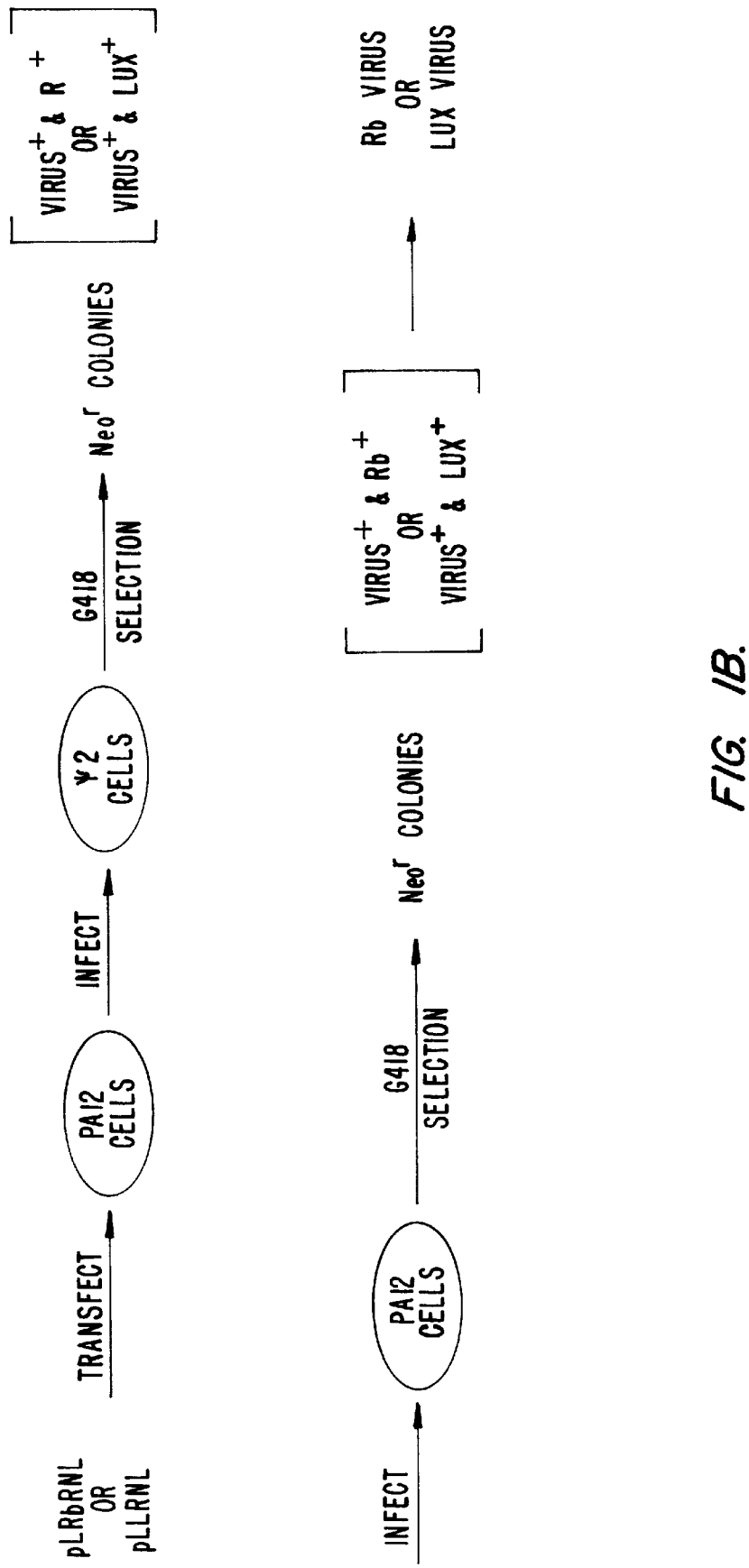

Now, with further reference to the figures, FIG. 1A discloses construction of Rb virus. Plasmids $p^{LLRNL}$ and pGem1:Rb4.7 were digested with restriction endonucleases as shown, and appropriate fragments were ligated to form pLRbRNL. Only selected restriction sites are shown (H, Hind III; C, Cla I; S, Sma I; Sc, Sca I; R, EcoR I). LTR, long terminal repeat of moloney murine leukemia virus; Lux, luciferase gene; RSV, Rous sarcoma virus promoter; Neo, Tn5 neomycin-resistance gene; Am$^r$, ampicillin resistance gene; Rb, RB cDNA (4757 bp); TGA, stop condon.

FIG. 1B relates to production of amphotropic Rb and Lux viruses. Plasmids pLRbRNL or PLLRNL were transfected into amphotropic packaging cell line PA12 by calcium-phosphate precipitation. Viral supernatants were harvested after 48 hours and used to infect ecotropic packaging cell line psi-2. After 3–4 weeks of G418 selection, resistant colonies were assayed for virus production by infecting 208F rat fibroblasts. RB or Lux gene expression in G418-resistant 208F colonies was analyzed by immunoprecipitation with anti-FRB antibody for the Rb virus, or by detection of luciferase activity for the Lux virus. Virus$^+$ and Rb$^+$ or lux$^+$ clones were selected as ecotropic stock lines. Viral supernatants were used to infect PA12 cells and amphotropic stock lines were isolated by repeating the process of G418 selection and analysis of neo$^r$ colonies for virus production and RB or Lux gene expression.

Figure 2B:
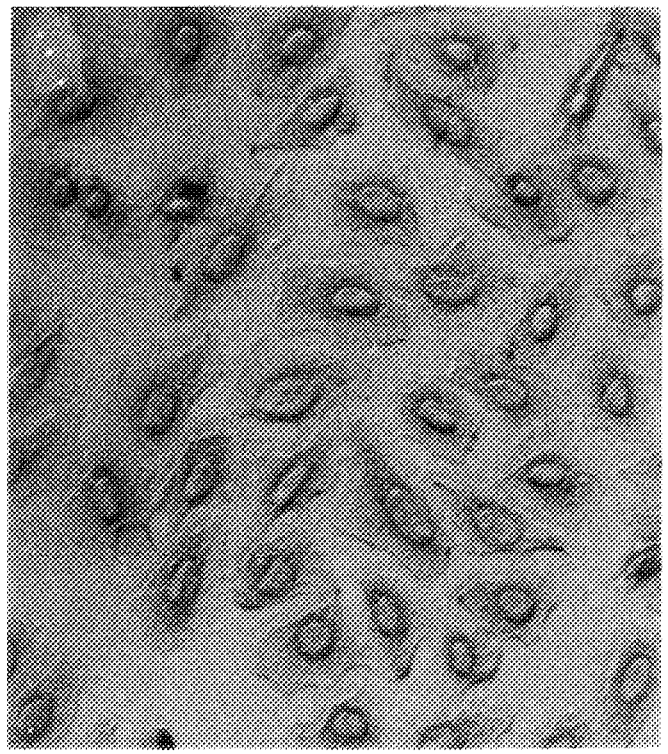
FIGS. 2B and 2C show photographs of indigenous RB proteins localized in the nucleus in U-20S cells.
Figure 2C:

FIGS. 2A and 2B depict expression of RB protein in Rb virus-infected retinoblastoma and osteosarcoma cell lines. In FIG. 2A, WERI=Rb27 (lanes 1 & 2), Saos-2 (lanes 3 & 4) and U-20S (lanes 5 & 6) cells were infected with Rb virus (lanes 2,4, & 6) or Lux virus (lanes 1,3,& 5) and grown in the presence of G418 (800 ug/ml for Saos-2 and U-20S and 1.0 mg/ml for WERI-Rb27) for 2 weeks (Saos-2 and U-20S) or 4 weeks (WERI-Rb27). Cells were then labeled with $^{32}$P-phosophoric acid (0.25 mCi/ml) for three hours. Cellular lysates were immunoprecipitated with rabbi anti-fRB IgG

(14) and analyzed on 7.5% SDS-polyacrylamide gels as described. RB protein (pp110$^{RB}$) is indicated.

In FIG. 2B, Saos-2 cells were infected with Lux virus (panel a) or Rb virus (panel b) and grown in G418-containing medium for 3 weeks in 60-mm dishes. Dishes were washed with PBS between each of the following steps: cells were fixed with 4% formaldehyde in 0.04M phosphate buffer (pH 7.4) for 20 minutes, and immersed in 1% $H_2O_2$ in 0.04M phosphate buffer for 10 minutes. Fixed cells were preincubated with normal goat serum for 10 minutes and then incubated with rabbit anit-fRB IgG diluted in 0.02% Triton X-100 overnight. After washing, biotinylated goat anti-rabbi IgG (TAGO, Burlingame, Calif.) was added to dishes. One hour later, cells were incubated with AB complex conjugated with horse radish peroxidase (Vector Labs, Burlingame, Calif.) for 30 minutes and then incubated with substrate (0.05% 3,3'-diaminobenzidine tetrahydrocholoride and 0.01% $H_2O_2$ in 0.05M Tris-HCl, pH7.6) (Polysciences, Inc.). Reactions were stopped 3–5 minutes later by washing cells with PBS> Cells were photographed with a Nikon diaphotomicroscope.

FIG. 3 depicts morphological effects of Rb or Lux virus infection in retinoblastoma and osteosarcoma cell lines. WERI-Rb27 (a & d), Saos-2 (b & e), and U20S (c & f) cells were infected with Lux virus (a–c) or Rb virus (d–f) and cultured in G418-containing media (concentrations as in FIG. 2A) for 8 weeks (WERI-Rb27) for 4 weeks (Saos-2 and U-20S). Cells were photographed in phase contrast with a Nikon diaphotomicroscope (magnification x 320 in all panels). The arrow points to an enlarged WERI-Rb27 cell while the arrowhead points to a normal-sized WERI-Rb27 cell.

FIG. 4 graphically illustrates the growth effects of Rb and Lux virus infection on retinoblastoma and osteosarcoma cells. Suspension cultures of WERI-Rb27 cells (A) were infected with Rb virus (squares) or Lux virus (circles) for 2 days and grown in the presence of G418 for 8 weeks. 1×10$^5$ cells were then seeded in 200 ul of culture medium in individual wells of 96-well microtiter plates (day 0). Three wells were harvested on each of day 1 to day 5 and counted in a hemacytometer. Average cell number/well (+1 S.D.) is shown. Monolayer cultures of Saos-2 (B) and U-20S (C) cells were infected with Rb virus (squares) or lux virus (circles) for two days, then plated in 60 mm dished and grown in G418-containing medium for 7 days. Similar numbers of neomycin-resistant colonies were present in each dish; about 50 randomly selected colonies were marked and the number of cells in each colony was determined under the microscope (day 1). Numbers of cells in the same colonies were measured during the next 4 days. Average cell number/colony (+1 S.D.) is shown. In dishes with Rb virus-infected Saos-2 cells, two subpopulations of colonies were clearly distinguished, one slow-growing (n=41, filled squares) and one fast-growing (n=6, empty squares); these were plotted separately.

In FIG. 5, RB gene expression in fast-growing Saos-2 colonies infected with Rb virus is depicted. Individual fast-growing Saos-2 colonies (lanes 1–9) were isolated and grown into mass cultures in G418-containing medium. These cells and U-20S cells (lane C) were labelled with $^{32}$p-phosphoric acid and cellular lysates were immunoprecipated as described in relation to FIG. 2A above. RB protein (ppRB$^{110}$) is indicated.

To test the influence of the RB protein on anchorage-independent growth, osteosarcoma cells infected with either Rb or Lux virus for their ability to grow in soft agar were assayed *J. Virol.* 38:1064 (1981). Different densities of cells were initially seeded and the numbers of resulting colonies were scored. As shown in Table 2, colony formation by Rb virus-infected Saos-2 cells was markedly reduced compared to uninfected or Lux virus-infected cells. In contrast, colony formation by U-20S cells did not vary significantly with regard to type of infection (Table 2). These data indicate that Saos-2 colonies formed in soft-agar could be derived from fast-growing cells. Therefore, anchorage-independent growth was retarded by exogenous RB protein in osteosarcoma cells lacking endogenous RB protein.

TABLE 2

Soft-agar colony formation of Rb or Lux virus-infected osteosarcoma cells.

| | Colony number of | | | | | |
|---|---|---|---|---|---|---|
| | Saos-2 | | | U-20S | | |
| cell number seeded | — | Lux | Rb | — | Lux | Rb |
| 1.0 × 10$^5$ | TMTC | 396 | 56 | 384 | 340 | 290 |
| 2.5 × 10$^4$ | 124 | 138 | 7 | 109 | 151 | 90 |

Cells infected with Rb or Lux virus were grown in G418-containing medium for 10 days. Viable G418-resistant and parental cells (–) were seeded in duplicate at various dilutions in 0.35% soft agar as described (24). Total colony numbers were scored after 20 days of growth. Individual colonies of Saos-2 contained more than 50 cells, whereas U-20S contained about 30 cells. TMTC: Too many to count.

An important experimental test of neoplastic behavior is the ability of injected cells to form tumors in nude mice. Conversely, loss of tumorigenicity is the most important validation for suppression of the neoplastic phenotype by the RB gene. WERI-Rb27 was considered a good candidate for the tumorigenicity assay, since it consistently formed tumors in nude mice three weeks after injection of 1–2×10$^7$ cells (Table 3).

On the other hand, Saos-2 and U-20S were only poorly tumorigenic. Two experiments were performed with WERI-Rb27 cells, one at three weeks and one at five weeks post infection with each virus in which 2×10$^7$ viable infected WERI-Rb27 cells were injected into the flanks of nude mice; right flanks was used for Rb virus-infected cells, and left flanks of the same mice were used as controls with Lux virus-infected tumor cells. Seven of seven mice formed tumors only on the left side (from Lux virus-infected cells), whereas zero of seven formed tumors on the right side (from Rb virus-infected cells) followed bilateral injections of WERI-Rb27 cells infected as above (Table 3). Thus exogenous RB protein demonstrably suppressed tumor formation in one highly tumorigenic retinoblastoma cell line. Rb virus infection severely retarded the growth rate of Saos-2 cultures, so it was impossible to accumulate sufficient numbers of infected cells for our assay.

These in vitro and in vivo results support the conclusion that replacement of the RB-tumor cells suppressed their neoplastic behavior, while tumor cells with apparently normal RB genes were not so affected.

TABLE 3

Tumorigenicity of RB or Lux virus-infected WERI - RB27 cells.

| | No. of Mice with tumor/No. or mice injected | | |
|---|---|---|---|
| Experiment # | Parental | Lux | Rb |
| 1 | 5/5 | 5/5 | 0/5 |
| 2 | — | 2/2 | 0/2 |

Cells infected with Rb or Lux virus were grown in G418-containing medium for 3 weeks (experiment 1) or 5 weeks (experiment 2). Cell viability was verified by trypan-blue exclusion, and $2 \times 10^7$ viable virus-infected cells were injected subcutaneously into either flank of the same nude-mouse. The same number of uninfected parental cells were injected into other mice. Tumor formation was scored after two months as presence or absence of a palpable tumor mass.
—: not done.

E6. USE OF THE RB GENE IN CANCER SUPPRESSION

Since two different meanings are attached to the term "cancer suppression", the following distinction may be drawn. Detection of inactivating mutations of the RB gene in natural human tumors supports the idea that the RB gene normally functions to "suppress" or "prevent" tumor formation in susceptible precursor cells. However, this does not necessarily imply that replacement of this gene would "suppress" or "revert" neoplastic cells to more normal behavior later in their evolution. For example, failure of the RB gene to suppress RB-tumor cells might be due to the acquisition of multiple additional alterations during oncogenesis. To test these possibilities, interventional experiments were conducted. In this initial study, a normal RB gene was introduced by viral mediated gene transfer into cultured human tumor cells that lacked endogenous RB protein. Suppression of the neoplastic phenotype was observed both by in vitro indices, such as soft agar colony formation, and by an in vivo assay, that of tumorigenicity in nude mice. Therefore, the cloned retinoblastoma gene indeed satisfied one definition of a human cancer suppressing gene: it functioned to suppress neoplastic behavior of certain tumor cells. As expected, no suppression effects of exogenous RB protein were observed in tumor cells that contained an intact endogenous RB gene.

Tests have established that the RB gene has a role in the suppressing of multiple types of human cancer. The RB gene was initially defined as the genetic element conferring susceptibility to hereditary retinoblastoma. Children surviving this form of retinoblastoma were highly predisposed to second primary tumors later in life, suggesting a broader role for the RB gene in other cancers *J. Cell. Biochem. in press* (1988). Mutations of the RB gene are often detected in retinoblastoma tumors; the most sensitive indicator is absence of RB protein, which has been observed in all retinoblastomas tested to date *Nature* 329:642 (1987). Using similar techniques, complete inactivation of the RB gene has also been found in a wide variety of nonretinoblastoma tumors such as osteosarcoma, synovial sarcoma and other soft tissue sarcomas, breast carcinoma and small cell lung carcinoma *Cancer Res.* 48:3939 (1988); *Hum. Pathol.* 19:487 (1988); *Proc. Natl. Acad. Sci.* 20 84:9059 (1987); *Science* 241:218 (1988); ibid 241:353 (1988); J. Y. Shew et al. unpublished. Thus, it has been demonstrated that a normal RB gene has cancer suppression activity not only in retinoblastoma cells but also in RB-osteosarcoma cells; similar effects have been observed in RB-breast cancer cells (E. Y.-H. P. Lee & W.-H. Lee, unpublished). In conjunction with observations of RB mutations in natural human tumors, these results support the conclusion that loss of this gene is a critical step, perhaps the initial step, in the genesis of several kinds of human cancer.

Pending U.S. patent application Ser. No. 108,748 discloses and claims the RB gene and its clone. The RB gene and its clone had the nucleotide sequence depicted in Table 2.

TABLE 4

| | |
|---|---|
| TTCCGGTTTTTCTCAGGGGACGTTGAAATTATTTTTGTAACGGAGTCGGGAGAGACGACGG GGCGTGCCCCGCCGCCGCCGGAACCCGCCGCCGCCGCCCCCGGGCTGCTCCTCCCACAGGTCGGTGGCTC | 120 |
| CGGCCGGGGAAAGGCGTCATGCCGCCCAAACCCCCGAAAAACGGCCGCCGCCGCCGGGGAG AACCCGCCGCCGCCGCCGGGGCTGCTCCCCCCCTGCGGCTGCTCCTCCACAGGTCGGTGGCTC | 240 |
|             [M] P P K T P P R K T [A A T A A A A A A] E [P P A P P P P P P] E E E D P P E | (34) |
| CAGGACAGGCCCGGAGGACCTGCCTCTCGTCAGGCTTGAGTTTGAAGAAACAGAAGAA CCTGATTTTACTGCATTATGTCAGAAATTAAGATACCAGATCATGTCAGAGAGAGCT | 340 |
| Q D S G P E D L P L V R L E F E E E T E E P D F T A L C Q K L K I P D H V R E R A | (74) |
| TGGTTAACTTGGGAGAAAGTTTCATCTGTGGATGGAGTATTGGGAGGTTATATTCAAAAG AAAAAGGAACTGTGGGGAATCTGTATCTTTATTGCAGTGAATGAGATGTCG | 480 |
| W L T W E K V S S V D G V L G G Y I Q K K K E L W G I C I F I A A V D L D E [M] S | (114) |
| TTCACTTTTACTGAGCTACAGAAACATATAGAAATCAGTGTCCATAAATTCTTTAACTTA CTAAAAGGAGAAGTTCTACAAGGGGAAGTTCTATGTCAAAGTGTGAAGAAG | 600 |
| F F T E L Q K H I E I S V H K F F H L L K E I D T S T K V D N A H S R L L K K | (154) |
| TATGATGTATTGTTTGCACTCTTCAGCAAATTGAAACATGTGAACTGTGAATTGATATATTG ACACAACCAGCAGTTCGATATCTCGAAATAAATTCTGAAAATGATAC | 720 |
| Y D V L F A L F S K L E R T C E L I Y L T Q P S S I S T E I N S A L V L K V S | (194) |
| TGGATCACATTTTTATTAGCTAAAGGGGAAGTATTACAAATGGAAGATGATCTGGTATTCAGT TTCCAATTGAAATGTGTACTATGTGGACTATATAAAGCTCCAGGTGGATGTGTG | 840 |
| W I T F L L A K G E V L Q M E D D L V I S F Q L N L C V L D Y F I K L S P P H L | (234) |
| CTCAAAGAACCATATAAAACAGCTGTTATACCCATTAATGGTTCACCTGAACAGGAGT GCACGGTGCAAAACAGTAGCAGAATAGCAAAACAACTAGAAAATGATAGAATTATT | 960 |
| L K E P Y K T A V I P I N G S P R T P R R G Q M R S A R I A K Q L E N D T R I I | (274) |
| GAAGTTCTGTAAAGAACATGAATGTAATATAGATGAGGTGAAAAATGTTTATTCCAAAA TTTATCCTTTCCATAATTCCCTGGACTTGTAACATCTAATGGAGTTCCAGAGGTT | 1080 |
| E V L C K E H E C N I D E V K N V Y F K N F I P F H N S L G L V T S N G L P E V | (314) |
| GAAAATCTTCTAAACGATACGAAGAAAATTTATCTTAAAAATAAGGATCTTGATGCAAGA CTTTTTCTTGATCATGATAAAACTCTTCAGACTGATTCTCTATAGACAGTTTGAAACACAG | 1200 |
| E N L S K R Y E E I Y L K N K D L D A R L F L D H D K T L Q T D S I D S F E T Q | (354) |
| AGAACACCAAGAAAAAGTAACCTTGATGAAGAGGTTAATGTAATTCCTCCACACACTCCA GTTAGGACTGTTATGAACACTATCCAACAATTAATGATTCATTAAATTCAGCAAGTGAT | 1320 |
| R T P R K S N L D E E V N V I P P H T P V R T V M N T I Q Q L M H I L N S A S D | (394) |
| CAACCTTCAGAAAATCTGATTTCCTATTTTCACTGCACAGTGAATACTGCAAAAGAGTGT TAAAAAGAGTTGTAAAGGACATTGGGCTATCTTCTAAAGAAACATTTCTTAAAGCTAAAGCAGTG | 1440 |
| Q P S E N L I S Y F H H C T V H P K E S I L K R V K D I G Y I F K E K F A K A V | (434) |
| GGACAGGGTTGTGTCGAAATTGGATCACAGCGATACAAACTTGGAGTTCGCTGTATTACC GAGTAATCAGAAGAACGATTATCCATTCAAATTTTAGCTCTAGCTG | 1560 |
| G Q G C V E I G S Q R Y K L G V R L Y Y R V M E S M L K S E E E R L S I Q N F S | (474) |
| AAACTTCTGAATGACAACATTTTTCATATGTCTTTATTGGCGCTGCAGGCTCTTGAGGTGT TAATGCACAAGTACATCTCAGAATCTTGGAACAGATTGTCTTTC | 1680 |
| K L N D N I F H M S L L A C A L E E V V M A T Y S R S T S Q N L D S G T D L S F | (514) |
| CCATGGATTCTGAATGTCTTTAAATTTGATTTTTACAAGCCTTTGATTTTTACAAAGTGAT CGAAACATTTAGAACGATGAAACATTTGAACAGATGAACCATCAACATTTAGAACAGATGACAACATTTAGA | 1800 |
| P W I L N V L N L K A F D F Y K V I E S F I K A E G N L T R E M I K H L E R G E | (554) |
| CATGGAATCATGGAATCCCTTGCAGTGGCTCTCAGATTCACCTTGATGATCTCATTATTAAA CAATCAAAGGACCGAGAAGGACCAACTGATCATCTTGAATCTGCATGTCCTAATCTT | 1920 |
| H R I M E S L A W L S D S P L F D L I K Q S K D R E G P T D H L E S A C P L N L | (594) |
| CCTCTCCAGAATAATCACACTGCTGCAGATATGTATCTTTCCCCTGTAAGATCTCCAAAAG AAAAAGGTTCAACTTACTGCGTGTAAATTCTACTGCAAATGCAGAGACACAAGCAACCTCA | 2040 |
| P L Q N N H T A A D M Y L S P V R S P K K K G S T T R V N S T A N A E T Q A T S | (634) |
| GCCTTCCAGACCCAGAAGCCATTGAAATCTACCTCTCTTTGATTTATAAAAAAGTGTATCGGCAAG CCTATCTCCGGCTAAATACACTTTGTGAACGCCTTCTGTGTGAGCACCCA | 2160 |
| A F Q T Q K P L K S T S L F Y K K V Y R L A Y L R L N T L C E R L L S E H P | (674) |

TABLE 4-continued

```
GAATTAGAACATATCATCTGGACCCTTTTCCAGCACACCCTGCAGAATGAGTATGAACTCATGAGAGACAGGCATTTGGACCAAATTATGATGTGTTCCATGTATGGCATATGCAAAGTG  2280
 E  L  E  H  I  I  W  T  L  F  Q  H  T  L  Q  N  E  Y  E  L  M  R  D  R  H  L  D  Q  I  M  M  C  S  M  Y  G  I  C  K  V   (714)
AAGAATATAGACCTTAAATTCAAATCATTGTAACAGCATACAAGGATCTTCCTCAGTGTTTCAGGAGACATTCAAACGTGTTTTGATCAAAGAAGAGTATGATTCTATTATAGTA  2400
 K  N  I  D  L  K  F  K  I  I  V  T  A  Y  K  D  L  P  H  A  V  Q  E  T  F  K  R  V  L  I  K  E  E  Y  D  S  I  I  V   (754)
TTCTATAACTCGGTCTTCATGCAGAGACTGAAAACAAATATTTTGCAGTATGCTTCCACCAGGCCCCCTACCTTGTCACCATTCCCACATTCTCACCATTCCAATACCCTGTCACCAGGCCCCCTACCTTGTCAGTATGCTTCCACCAGGCCCCCTACCTTGTCAGTATGCTTACAAGTTTGGTAGT  2520
 F  Y  N  S  V  F  M  Q  R  L  K  T  N  I  L  Q  Y  A  S  T  R  P  P  T  L  S  P  I  P  H  I  P  R  S  P  Y  K  F  P  S   (794)
TCACCCTTACGGATTCCTGGAGGGAACATCTATATTTCACCCCTGAAGAGTCCATATAAAATTTCAGAAGGTCTGCCAACACCAACAAAATGACTCCAAGATCAAGAATGTTAGTATCA  2640
 S  P  L  R  I  P  G  G  N  I  Y  I  S  P  L  K  S  P  Y  K  I  S  E  G  L  P  T  P  T  K  M  T  P  R  S  R  I  L  V  S   (834)
ATTGGTGAATCATTCGGGACTTCTGAGAAGTTCCAGAAAATAAATCAGATGGTATGTAACAGCGACCGTGTCTCAAAAGAAGTGCTGAAGCAACCTCTAAACCAGTGAAAAAA  2760
 I  G  E  S  F  G  T  S  E  K  F  Q  K  I  N  Q  M  V  C  N  S  D  R  V  L  K  R  S  A  E  G  S  N  P  P  K  P  L  K  K   (874)
CTACGCTTTGATATTGAAGGATCAGATGAAGCAGATGGAAGTAAACATCTCCCAGGAGAGTCCAAATTTCAGCAGAAGTTCTACTGAACACGAATGCAAAAGCAG  2880
 L  R  F  D  I  E  G  S  D  E  A  D  G  S  K  H  L  P  G  E  S  K  F  Q  Q  K  L  A  E  M  T  S  T  R  T  R  M  Q  K  Q   (914)
AAAATGAATGATAGCATGGATACCTCAAACAAGGAAGAAAATGAGGATCTCAGGATTCATTGTCTCTCCACAGATGTGACTGTAT...to  4757
 K  M  N  D  S  M  D  T  S  N  K  E  E  K                                                                                  (928)
```

E3. SUPPRESSION OF ONCOGENICITY IN VITRO AND IN VIVO BY THE RB GENE (a) Expression vectors containing functional RB cDNA clones were prepared as follows: A full-length 4.7 kb RB cDNA was constructed from three overlapping cDNA sequences, RB-1, RB-5, and Y79RB. This cDNA is placed under the control of either SV40 early gene promotor or LTR of Moloney murine leukemia virus and is inserted into a retroviral vector (MuLV-LTR-neo).

(b) Production of RB-virus: Infectious viruses containing RB genes are made from packaging cell lines 2 after viral DNA-calcium phosphate coprecipitation in the presence of polybene. Forty eight hours later, the supernatant containing ecotropic RB-neo virus is harvested and used to infect pA12 cells, which is another helper line providing amphotropic envelop protein. While only a small fraction of pA12 cells are infected with ecotropic RB-neo virus, the positively infected pA12 cells are enriched under the G418 selection for the neo-resistant phenotype. Viral particles released from infected pA12 cells are pseudotypic with amphotropic envelop proteins and are able to infect species beside rodents. The virus can be checked for the presence of the RB gene by either hybridizing with RB probe or by its ability to express RB proteins.

(c) Phenotypic changes of retinoblastoma cells by RB gene: Several lines of retinoblastoma cells, such as Y79 or WERI-1, can produce palpable tumors in nude mice within 4 weeks. These cells were infected with infectious virus containing the functional RB gene and then assayed for their tumorigenicity. Meanwhile, the expression of RB gen in these infected cells was checked. LTR-neo virus carrying only neo genes were used as control. In addition, the infectious RB-virus was directly inoculated into established retinoblastoma tumors in nude mice and the suppression of tumor growth examined.

E4. TRANSFORMATION BY INACTIVATION OF RB GENES (a) Infectious virus containing defective RB sequences were constructed similar to the procedures described above and used for targeted mutagenesis of the endogenous RB gene.

(b) Fibroblasts from retinoblastoma patients, such as GM 1142 and S-362, contained only a single copy of the functional RB gene and were used as target cells for the inactivation of RB gene by homologous recombination. Colonies resistant to G418 are characterized according to the following parameters; (1) insertion site; (2) expression of RB proteins; and (3) transforming phenotype both in vivo and in vitro.

A view of the cancer suppressing characteristics of the RB gene, the use of the gene or its clone as a pharmaceutical has been established. In addition, the RB gene may be used for prophylactic prenatal and postnatal screening, and for prediction of the development of secondary cancer, such as osteosarcoma, fibrosarcoma, glioblastoma, breast cancer, and others, whether or not connected with retinoblastoma.

It will be recognized that another use is the suppression of cancer growth by providing RB gene cDNA directly to the tumor cells, which cells in turn will product ppRB$^{110}$ which will effect the other tumorous cells.

Although diagnostic and prophylactic methods with regard to the RB gene have been described, it must be understood that the present invention is intended to cover the use of any replacement gene as a pharmaceutical to treat animals, including humans, who have a cancerous condition or who have inactive, mutated or defective cancer suppressing genes. Injecting, treating, or by other appropriate means, the animal having a defective gene with its identical or nearly identical natural or cloned non-defective gene or gene fragment to treat and/or prevent cancer is what is intended by this invention.

F. ANIMAL MODELS FOR EVALUATING SUSPECTED ENVIRONMENTAL INFLUENCE CARCINOGENICITY

In order to determine carcinogenicity of suspected environmental influences, the cancer suppressing gen of an animal model is controlled by genetic manipulation to render it susceptible to carcinogenic influences. In this regard, one of a pair of cancer suppressing genes of the animal is rendered inactive, so that the offspring of the animal may be exposed to the expected environmental carcinogen for testing purposes.

Tumor development of the animal thus exposed is a positive indication of carcinogenicity of the suspected environmental influence.

As an example of production of a mouse model for evaluation of carcinogenicity of suspected environmental influences, a strain of mice had been developed having heterogenicity of the RB gene. Exposure of the mouse to a carcinogen results in alteration of the dominant RB gene thereby resulting in production of the homozygous, recessive condition with attendant tumor development.

Understanding the molecular basis for transforming a normal cell into a tumor cell is a major challenge for scientists studying tumorigenesis. For many experimental tumors, multiple stages of carcinogenesis have been demonstrated *Nature,* 315:190, (1985). Recent studies have shown that activations of oncogenes might be involved in the initiation of carcinogenesis, and multiple oncogenes might be required in the process of immortalization of normal cells and the expression of transforming phenotype *Nature* 304:596, (1983). Generally, these oncogenes are dominantly acting genes and the expressions of these genes products in excess quantity or in altered form are necessary for malignant transformation.

A major paradox in cancer biology arises from studies with cell hybridization between normal and malignant cells. It has been shown that the tumorigenic activity of malignant cells can be suppressed by genes or chromosomes from normal cellsand the malignancy of the hybrid cell reverts after loss of DNA from normal cells. *Adv. Cancer Res.,* 44:43, (1985). This suggest that tumorigenicity is recessive in nature and inactivation of these "tumor suppressing genes" may also be involved in the initiation of human tumorigenesis *Science,* 238:1539, (1987).

Karyotypic examination of somatic cells (fibroblasts) from patients with hereditary retinoblastoma has shown visible deletions of the long arms of chromosome 13 in some cases Birth Defects, 12:131, (1976). Similar defections were observed in retinoblastoma tumor cells *Cancer Genet. Cytogenet.* 6:213, (1982). Band q14 was common among all deletions and presumably contains a hypothetical gene (RB) determining the susceptibility to hereditary retinoblastoma. Based on the clinical observation, it has been suggested that initiation of tumorigenesis can result from as few as two mutation events and that retinoblastoma arises by the loss of both alleles at the same locus *Proc. Natl. Acad. Sci. U.S.A.,* 68:820, (1971); *Cancer,* 35:1022, (1975). Consequently, the presence of the hypothetical gene product would prohibit or suppress tumorigenesis while loss of the gene function will result in malignant growth.

A gene on chromosome 13 has been identified as the RB gene *Science,* 235:1394, (1987); *Nature,* 323:643, (1986). It encoded a 4.7 kb mRNA transcript, expressed in most normal cells including fetal retina. Partial or complete deletion of this gene were detected in 2 of 6 retinoblastomas examined while 4 had apparently intact genes. However, the RB mRNA was altered in 6 of 6 retinoblastomas examined and the changes included either expression of shortened mRNA message (4.0 kb instead of 4.7 kb) or absent expression. Complete loss of RB gene function in retinoblastomas was further confirmed at the level of protein translation *Nature,* 329:642, (1987).

Antibody raised against a segment of the RB gene product can immunoprecipitate a protein of 110 kd in normal cells and many non-retinoblastoma tumor cells. However, this 110 kd protein was absent in 5 of 5 retinoblastomas examined. This suggests its importance in the oncogenesis of retinoblastoma. Furthermore, this protein was found to be a phosphoprotein with DNA binding activity and located in the nucleus thereby suggesting its regulatory roles in the expression of genes. As discussed above, the phosphoprotein has been identified as $ppRB^{110}$.

Further genetic identification of the RB gene can be confirmed by its expected biological functions. Two basic questions can be addressed: 1) Whether oncogenicity of retinoblastoma cells is suppressed by the presence of functional RB gene products; and 2) Whether the absence of the functional RB gene results in the malignant phenotype. Introduction of chromosome 11 into Wilm's tumor cells resulted in the suppression of tumorigenicity in nude mice although these cells remained morphologically transformed in tissue culture *Science,* 236:175, (1987).

Of interest, also, is whether the single RB gene can suppress the tumorigenicity of retinoblastoma cells. Targeted mutagenesis by homologous recombination has been used successfully in inactivation of the myosin heavy chain gene in *Dictyosteliym discoideum Science,* 236:1086, (1987). Targeted mutagenesis with homologous recombination has also been shown in diploid cells as well as mouse embryonic stem cells *Cell,* 44:419, (1986); *Cell,* 51:503, (1987). Therefore, inactivation of the RB gene by targeted mutagenesis provides important information about its role in the regulation of cell growth and its oncogenic potential. In addition, the roles of the RB gene in the oncogenesis of second primary tumors in retinoblastoma patients can be studied by these methods.

In order to study RB gene function, an animal model was prepared. Two potential animal models for Lesch-Nyhan syndrome have been developed. *Nature,* 326:292, (1987). *Nature,* 326:295, (1987) Both mouse model systems were derived by construction of chimeric mice with HPRT-mutagenized mouse embryonic carcinoma (EC) or embryonic stem (ES) cells which can give rise to germ cells in chimeras. These chimeras allow the derivation of strains of mutant mice having the same biochemical defect as Lesch-Nyhan patients. The objective was to utilize either mouse ES or EC cells to establish chimeric mice with one inactive allele of the RB gene.

Either mouse ES or EC cells were used to establish chimeric mice with one inactive allele of RB gene for studying its biological significance. One allele of the RB gene of the mouse ES cell (rb/rb) was inactivated by targeted mutagenesis with a viral vector containing defective RB sequences. Another selection marker, which aligns in frame with the RB gene but is inactive in defective RB-virus, was incorporated for selection purposes.

After homologous recombination with endogenous RB, the marker expressed under the control of endogenous RB regulatory sequence and was selected along with neo-resistancy. The neomycin-resistant ES cell were further examined for the rb/−) genotype by DNA hybridization with RB probe and were injected into mouse blastocyctes to construct chimeric animals *Proc. Natl. Acad. Sci. U.S.A.,* 83:9065, (1986).

The resulting chimeric mice are bred to maintain a colony before sacrificing and examination for the (rb/−) phenotype of the primary fibroblast.

The invention of the animal model for studying cancer suppressing gene function is now presented in greater detail. Two potential animal models for Lesch-Nyhan syndrome were developed. Both mouse model systems were derived by construction of chimeric mice with HPRT-mutagenized mouse embryonic carcinoma (EC) or embryonic stem (ES) cells which can give rise to germ cells in chimeras. These allow the derivation of strains of mutant mice having the same biochemical defect as seen in Lesch-Nyhan patients. In the present invention, mouse ES cells were used as the target for RB gene inactivation via homologous recombination.

The expressions of the RB gene in different tissues of the mouse were examined by either Northern blotting of the poly(A) RNAs with mouse DNA probes or immunoprecipitation of mouse RB proteins with RB specific antibody. The expression of RB gene in ES cells as well as fetal retinal cells were the main targets of investigation.

One allele of the RB genes of the mouse ES CELL (rb/rb) was inactivated by targeted mutagenesis with DNA fragments containing defective RB sequences. Previously, the mouse RB cDNA has been isolated using the human RB cDNA as probe. Several mouse genomic DNA clones were isolated from a mouse genomic library by screening with mouse cDNA probe. These mouse genomic clones were used to construct the DNA fragment containing an inactivated RB coding sequence.

Basically, a neomycin resistant gene derived from Tn5 was inserted into mouse genomic DNA fragments of 5.6 and 10 kb with neomycin and/or G418 used for selection. In general, two types of vectors may be used for the targeted mutagenesis, based on the mode of action of homologous recombination. The first is a replacement vector carrying homologous sequences of the same orientation at each end of the vector and which results in an exact copy of the gene with internal $neo^r$ gene. The other is an insertional vector carrying homologous sequences of opposite orientation at each ends of the vector. However, the original DNA reading frame will be continued if this DNA fragment is circlized. When this vector was inserted into the exact position of the endogenous RB gene, an internal duplication of part of the RB was established, and thus, inactive RB gene was produced. Both types of vectors were constructed and the inactivation of RB genes in ES cells was accomplished by both approaches.

It was found that the vectors introduced into the ES cells either randomly integrate into the chromosome or specifically integrate into the RB loci. This fact creates difficulty for the selection of exact homologous recombinants or for simple neomycin resistant phenotype selection. Thus, another selection marker was incorporated for selection purposes.

Studies have shown that incorporation of herpes simplex viral tk gene into the targeted mutagenesis vector described above was beneficial. Basically, the HSV tk gene was linked to the end of a linearized vector. If the random integration of the tk-vector occurred, the tk gene would be carried over into the integration site. However, site specific homologous recombination can only occur after loss of the terminal tk sequence.

Recent development of compounds, such as acyclovir and ganciclovir, has provided an excellent selection system for cells with or without the tk gene *Antimicrob. and Chemother.*, 31:844–949 (1987). Therefore, ES cells with neo(+) and tk(−) were selected out by addition of G418 and ganciclovir respectively. Vectors with and/or without tk gene were both used to test their targeted mutagenesis efficiency. The neomycin-resistant ES cell was further examined for (rb/−) genotype by DNA hybridization with an RB probe.

Mouse ES cells thus mutated were screened for the detection of one inactive RB allele and one active allele of RB gene by RFLP analysis as well ploymerase chain reaction analysis. RB(+/−) ES cells obtained were reintroduced by microinjection into blastocysts (early embryo) obtained from superovulated female mice. The blastocysts carrying the RB (+/−) ES cells were then transplanted back to the uterus of a pseudopregnant female mouse *Proc. Natl. Acad. Sci. U.S.A.* 83:9065, (1986). After the foster mother mouse gave birth, the offspring were examined for the hereditary transmission of the mutationally inactivated RB allele.

The animal models developed according to the present invention are useful for the evaluation of suspected carcinogenicity of environmental substances. Because tumorigenicity is observed only when at least one of the cancer suppressing genes at a given locus is defective, mutated or missing, tumor development in the animal after exposure to the environmental substance is a positive indication of carcinogenicity for the substance.

In addition to their value in testing for substance carcinogenicity, the chimeric animal is useful for evaluating the pharmaceutical effect of the RB gene and RB gene products. It has been found that the administration of the RB gene and/or RB gene products to the healthy cell has no discernible adverse side effects. Thus, the RB gene and/or its products can be administered to organisms to correct a genetic deficiency while the risk of undesirable reactions has been reduced.

As used in this specification, the terms "defective" and "inactive" when referring to a gene, are intended to mean the condition wherein the gene expresses an abnormal phenotype or no phenotype.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. An isolated nucleic acid molecule comprising a nucleotide sequence encoding a full length human wild type RB protein, as shown in FIG. 6.

2. The isolated nucleic acid molecule of claim 1, wherein the nucleotide sequence is as shown in FIG. 6.

3. An isolated nucleic acid vector suitable for transfecting mammalian cancer cells, the vector comprising transcription regulatory sequences operably linked to a nucleotide sequence encoding a full length human wild type RB protein, as shown in FIG. 6.

4. The vector of claim 3, wherein the nucleotide sequence is as shown in FIG. 6.

5. The vector of claim 3, which is a virus.

6. The vector of claim 3, which is complexed with a liposome.

* * * * *